United States Patent
Trippier et al.

(10) Patent No.: US 11,369,593 B2
(45) Date of Patent: Jun. 28, 2022

(54) FUNCTIONALIZED PYRIDINE CARBAMATES WITH ENHANCED NEUROPROTECTIVE ACTIVITY

(71) Applicant: Texas Tech University System, Lubbock, TX (US)

(72) Inventors: Paul Trippier, Papillion, NE (US); Nihar Kinarivala, Jersey City, NJ (US); Rose-Mary Boustany, Beirut (LB)

(73) Assignee: Texas Tech University System, Lubbock, TX (US)

( * ) Notice: Subject to any disclaimer, the term of this patent is extended or adjusted under 35 U.S.C. 154(b) by 93 days.

(21) Appl. No.: 16/630,522

(22) PCT Filed: Jul. 13, 2018

(86) PCT No.: PCT/US2018/042009
§ 371 (c)(1),
(2) Date: Jan. 13, 2020

(87) PCT Pub. No.: WO2019/014547
PCT Pub. Date: Jan. 17, 2019

(65) Prior Publication Data
US 2021/0023064 A1    Jan. 28, 2021

Related U.S. Application Data

(60) Provisional application No. 62/532,624, filed on Jul. 14, 2017.

(51) Int. Cl.
| | | |
|---|---|---|
| A61K 31/44 | (2006.01) |
| A61K 31/325 | (2006.01) |
| A61K 31/4436 | (2006.01) |
| A61K 31/5377 | (2006.01) |

(52) U.S. Cl.
CPC ............ *A61K 31/44* (2013.01); *A61K 31/325* (2013.01); *A61K 31/4436* (2013.01); *A61K 31/5377* (2013.01)

(58) Field of Classification Search
None
See application file for complete search history.

(56) References Cited

U.S. PATENT DOCUMENTS

| | | | |
|---|---|---|---|
| 3,513,171 A | 5/1970 | Thiele et al. |
| 4,554,281 A | 11/1985 | Vonbebenburg et al. |
| 5,384,330 A | 1/1995 | Dieter et al. |
| 5,721,258 A * | 2/1998 | Schwarz ............... A61K 31/44 |
| | | | 514/352 |
| 6,117,900 A | 11/2000 | Rundfeldt et al. |
| 9,517,223 B2 | 12/2016 | Woolf et al. |
| 2010/0323016 A1 | 12/2010 | Nadjsombati |
| 2015/0190363 A1 | 7/2015 | Woolf et al. |

FOREIGN PATENT DOCUMENTS

| | | |
|---|---|---|
| CA | 2550023 A1 | 6/2005 |
| DE | 1795858 B1 | 4/1978 |
| EP | 1407768 A2 | 4/2004 |

OTHER PUBLICATIONS

Kinarivala et al, J. Med. Chem, 59,4415-4427 (Year: 2016).*
Dhar, Sumeer et al. "Flupirtine blocks apoptosis in Batten patient lymphoblasts and in human postmitotic CLN3—and CLN2-deficient neurons" Annals of Neurology Mar. 19, 2002 [abstract].
Emig, P., et al, 'New central analgesic-acting triaminopyridines'. Arzneimittel-Forschung, 1993, vol. 43, No. 6, pp. 627-631 [Abstract].
Harish, S. et al. "Flupirtine: Clinical Pharmacology" J. Anaesthesiol Clin. Pharmacol. Apr.-Jun., 2012.
International Search Report and Written Opinion (PCT/US2018/042009) [AU/ISA] dated Oct. 2, 2018.
Kinarivala, N., et al, "Discovery of Aromatic Carbamates that Confer Neuroprotective Activity by Enhancing Autophagy and Inducing the Anti-Apoptotic Protein B-Cell Lymphoma 2 (Bcl-2)". Journal of Medicinal Chemistry, Nov. 7, 2017, vol. 60, No. 23, pp. 9739-9756.
Reed, Nicholas Lawrence "Synthesis of Retigabine Analogues for the Treatment of Tinnitus and Progress Towards a Concise Route to XJB-5-131" Master's Thesis Nov. 18, 2014.

* cited by examiner

*Primary Examiner* — Zinna Northington Davis
(74) *Attorney, Agent, or Firm* — Edwin S. Flores; Daniel J. Chalker; Chalker Flores, LLP

(57) ABSTRACT

The present invention includes compositions and methods for treating a subject afflicted with a neurodegenerative disorder or disease by determining that the subject is in need of treatment for the neurodegenerative disorder or disease; and administering to the subject an amount of an effective amount of a compound comprising a flupirtine derivative as disclosed herein.

11 Claims, 5 Drawing Sheets

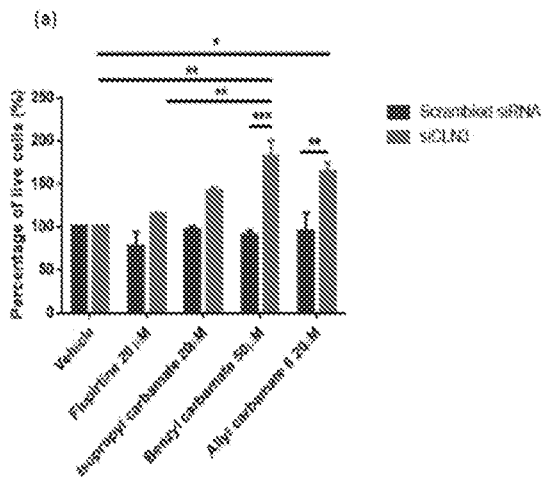
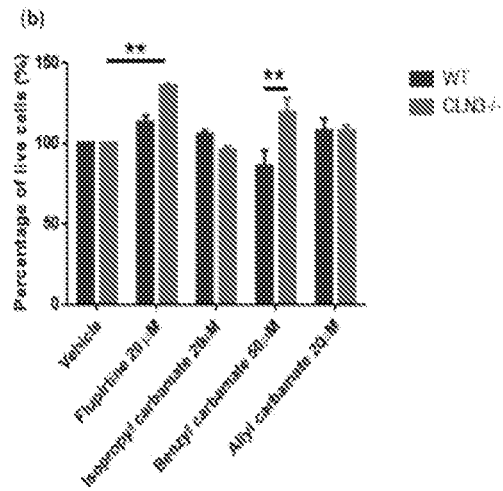
FIG. 3A  FIG. 3B
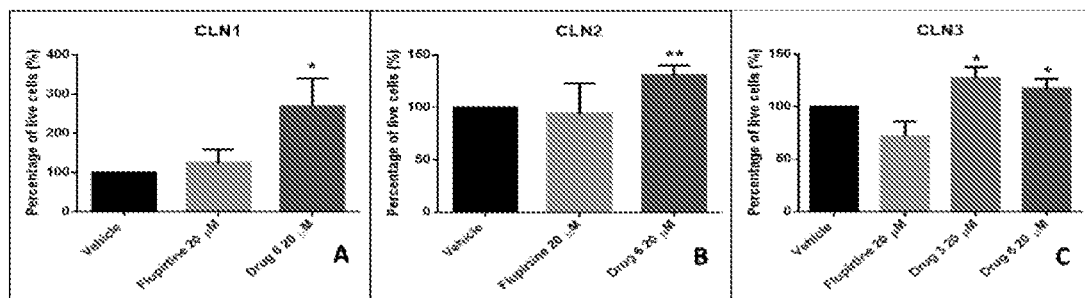
FIG. 4A  FIG. 4B  FIG. 4C
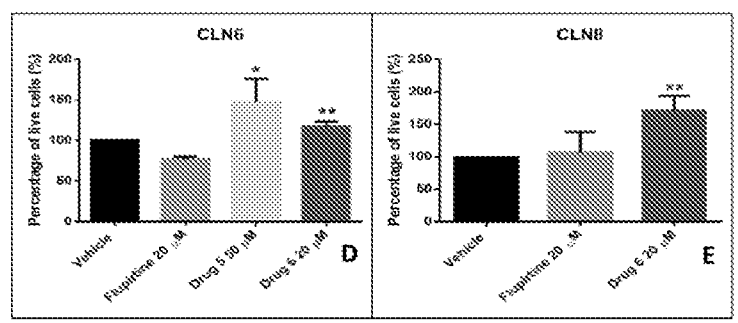
FIG. 4D  FIG. 4E

FUNCTIONALIZED PYRIDINE CARBAMATES WITH ENHANCED NEUROPROTECTIVE ACTIVITY

CROSS-REFERENCE TO RELATED APPLICATIONS

This application is the National Stage of International Application No. PCT/US2018/042009, filed on Jul. 13, 2018 claiming the priority of U.S. Provisional Application No. 62/532,624, filed on Jul. 14, 2017, the content of each of which is incorporated by reference herein.

TECHNICAL FIELD OF THE INVENTION

The present invention relates in general to the field of functionalized pyridine carbamates and their use in neuroprotective activity.

BACKGROUND OF THE INVENTION

Without limiting the scope of the invention, its background is described in connection with neuroprotection.

The non-opioid analgesic Flupirtine is a lead compound for neurodegenerative disease drug discovery and target identification. Flupirtine aborts etoposide and serum starvation-induced apoptosis in neuron-like PC12 cells, isolated hNT neurons with deficient CLN2 or CLN3 expression and furthermore, in phenotypic CLN2 and CLN3 deficient patient lymphoblasts. A mechanism of action involving, in part, induction of the apoptosis suppressor Bcl-2 has been proposed. Clinically approved monoamine oxidase inhibitors are known to induce Bcl-2, demonstrating that the upregulation of this protein provides no known adverse effects. Additionally, flupirtine treatment of Creutzfeld-Jakob disease patients results in cognitive gains in those treated and shows protective activity at 1 µg/mL to reduce apoptotic cell death caused by Abeta 25-35 (the etiological agent of Alzheimer's disease) in primary neurons. Both flupirtine, and its bioisostere retigabine, have shown efficacy in ALS patient induced pluripotent stem cells (iPSCs), with retigabine entering Phase I clinical trial at MGH. Despite this potential, studies aimed at optimizing and enhancing flupirtine or retigabine activity within a Batten disease phenotypic cellular model or any neurodegenerative disease and identifying their target of action have not been performed.

Flupirtine is known to function at several biological targets including activation of potassium channels, NMDA receptor antagonism, increasing glutathione levels and delaying loss of intermitochondrial membrane calcium retention capacity. The compound also acts as an antioxidant, and is widely known to be neuroprotective. Despite all of the known effects of flupirtine, the target of action that results in neuroprotection in CLN2 and CLN3 cellular models of Batten disease is as yet unknown. In a follow-up (non-clinical trial) study to assess the effect of flupirtine in NCL patients, a survey was conducted among parents of patients who were undergoing treatment with flupirtine. Parents reported a beneficial effect from flupirtine however, statistical analysis showed no difference between treatment and control groups. The initial study reported neuroprotective activity in vitro at concentrations >20 µM, a concentration difficult to achieve and maintain in vivo, suggesting more potent compounds could provide significant in vivo effect.

However, despite the availability of flupirtine and retigabine for decades, a need remains for improved drugs that can be used to treat neurodegenerative diseases.

SUMMARY OF THE INVENTION

In one embodiment, the present invention includes a method of treating a subject afflicted with a neurodegenerative disorder or disease comprising: determining that the subject is in need of treatment for the neurodegenerative disorder or disease; and administering to the subject an amount of an effective amount of a compound comprising a flupirtine derivative selected from at least one of:

Table of Compounds:

NK-3-1

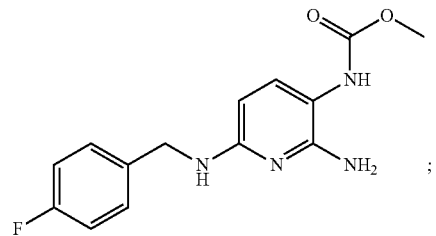 [SMILES: COC(=O)Nc1ccc(NCc2ccc(F)cc2)nc1N]

NK-4-3

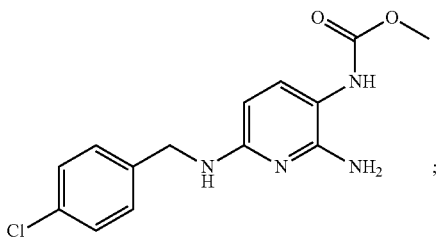 [SMILES: COC(=O)Nc1ccc(NCc2ccc(Cl)cc2)nc1N]

-continued
Table of Compounds:
NK-8-1
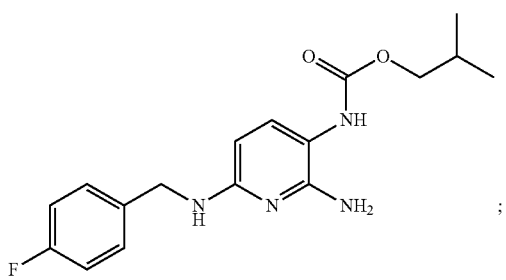 [SMILES: CC(C)COC(=O)Nc1ccc(NCc2ccc(F)cc2)nc1N]
;
NK-10-1
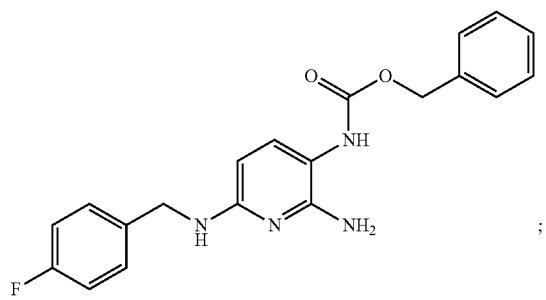 [SMILES: Nc1nc(NCc2ccc(F)cc2)ccc1NC(=O)OCc1ccccc1]
;
NK-12-1
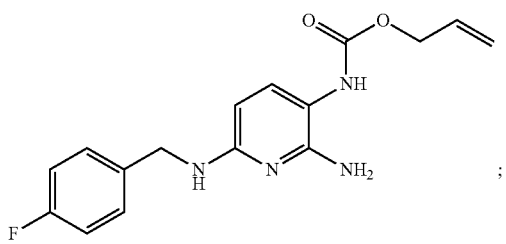 [SMILES: C=CCOC(=O)Nc1ccc(NCc2ccc(F)cc2)nc1N]
;
NK-13-1
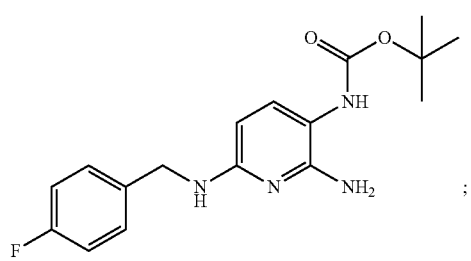 [SMILES: CC(C)(C)OC(=O)Nc1ccc(NCc2ccc(F)cc2)nc1N]
;
NK-16-3
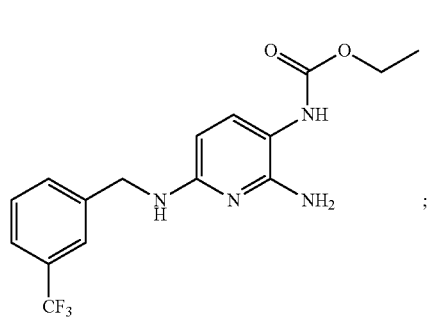 [SMILES: CCOC(=O)Nc1ccc(NCc2cccc(C(F)(F)F)c2)nc1N]
;

-continued
Table of Compounds:
NK-16-4
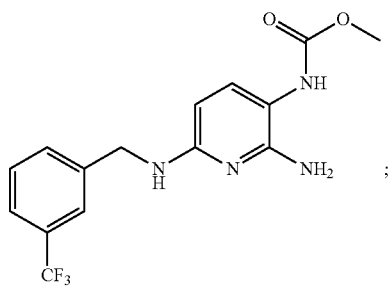 [SMILES: COC(=O)Nc1ccc(NCc2cccc(C(F)(F)F)c2)nc1N]
NK-16-6
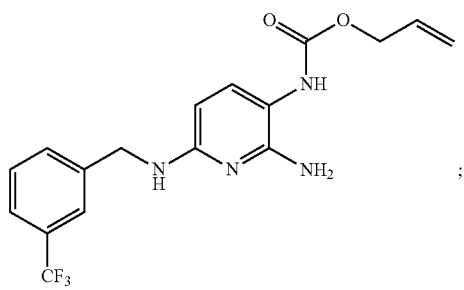 [SMILES: C=CCOC(=O)Nc1ccc(NCc2cccc(C(F)(F)F)c2)nc1N]
NK-17-3
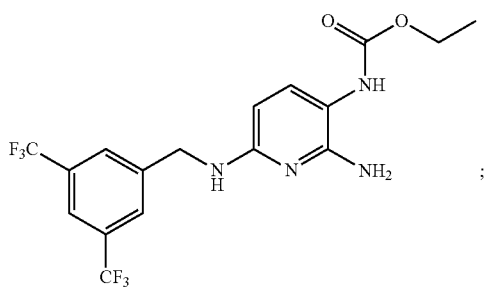 [SMILES: CCOC(=O)Nc1ccc(NCc2cc(C(F)(F)F)cc(C(F)(F)F)c2)nc1N]
NK-21-1
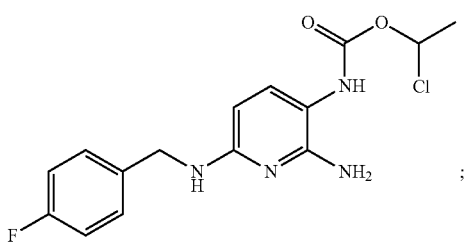 [SMILES: CC(Cl)OC(=O)Nc1ccc(NCc2ccc(F)cc2)nc1N]
NK-22-6
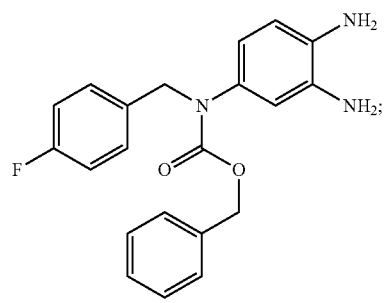

-continued
Table of Compounds:
NK-22-13 (Ref)
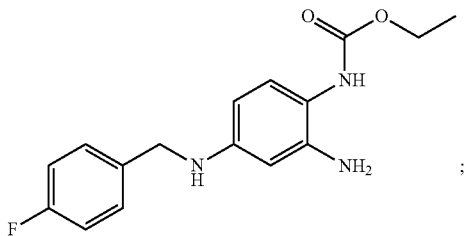 [SMILES: CCOC(=O)Nc1ccc(NCc2ccc(F)cc2)cc1N]
;
NK-23-1
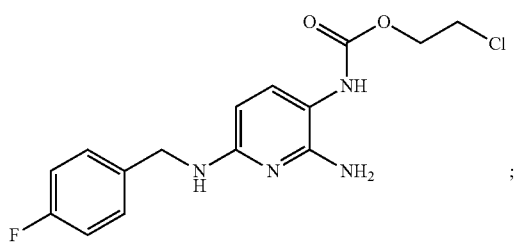 [SMILES: Nc1nc(NCc2ccc(F)cc2)ccc1NC(=O)OCCCl]
;
NK-30-2
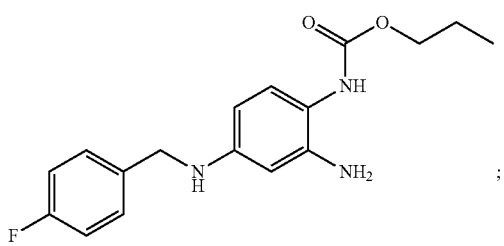 [SMILES: CCCOC(=O)Nc1ccc(NCc2ccc(F)cc2)cc1N]
;
NK-31-3
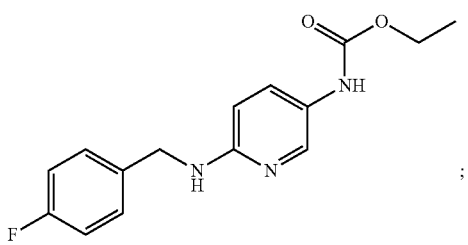 [SMILES: CCOC(=O)Nc1ccc(NCc2ccc(F)cc2)nc1]
;
NK-34-2
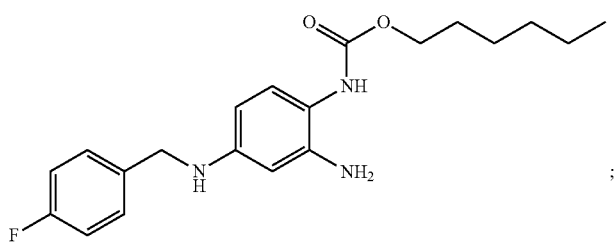 [SMILES: CCCCCCOC(=O)Nc1ccc(NCc2ccc(F)cc2)cc1N]
;
NK-39-3
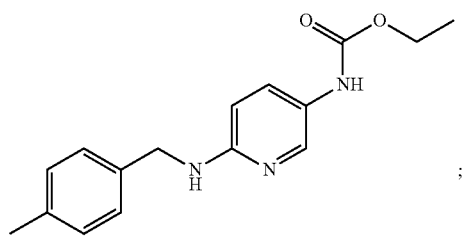 [SMILES: CCOC(=O)Nc1ccc(NCc2ccc(C)cc2)nc1]
;

-continued
Table of Compounds:
NK-40-3
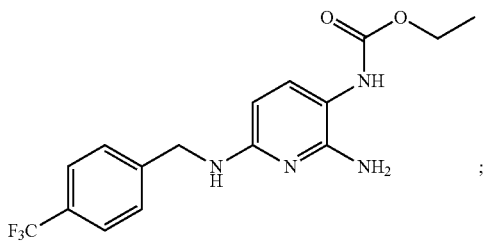 [SMILES: CCOC(=O)Nc1ccc(NCc2ccc(C(F)(F)F)cc2)nc1N]
NK-41-1
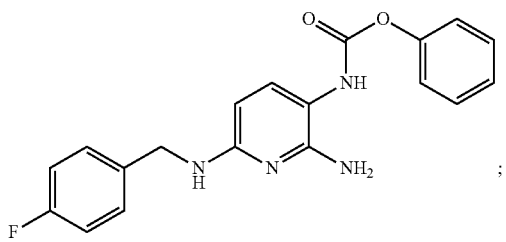 [SMILES: Nc1nc(NCc2ccc(F)cc2)ccc1NC(=O)Oc1ccccc1]
NK-42-1
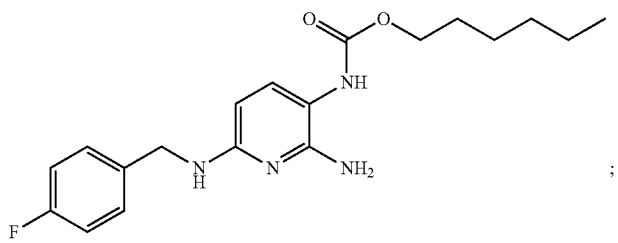 [SMILES: CCCCCCOC(=O)Nc1ccc(NCc2ccc(F)cc2)nc1N]
NK-43-1
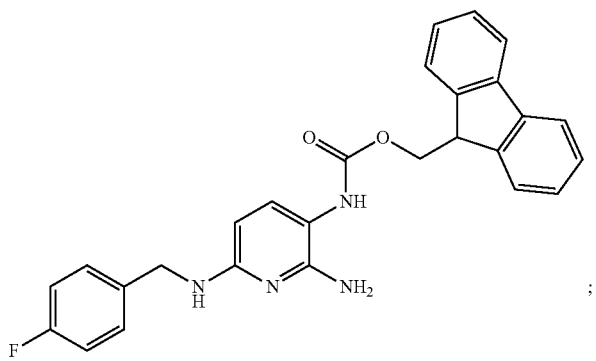 [SMILES: Nc1nc(NCc2ccc(F)cc2)ccc1NC(=O)OCC1c2ccccc2-c2ccccc21]
NK-45-1
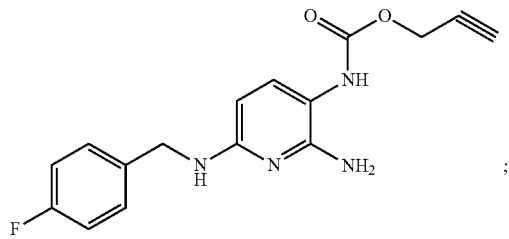 [SMILES: C#CCOC(=O)Nc1ccc(NCc2ccc(F)cc2)nc1N]

| Table of Compounds: | |
|---|---|
| NK-46-1 | 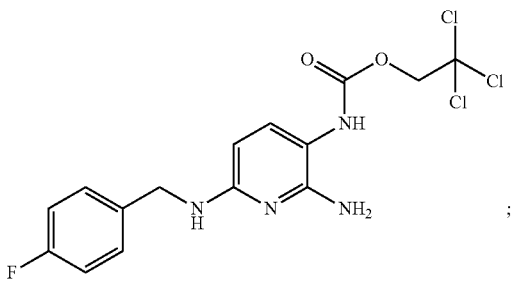 [SMILES: Nc1nc(NCc2ccc(F)cc2)ccc1NC(=O)OCC(Cl)(Cl)Cl] ; |
| NK-52-3 | 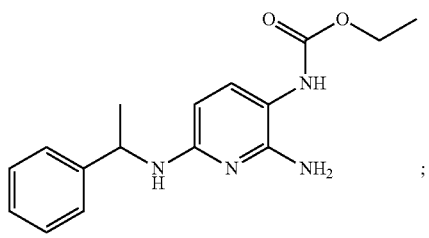 ; |
| NK-57-3 | 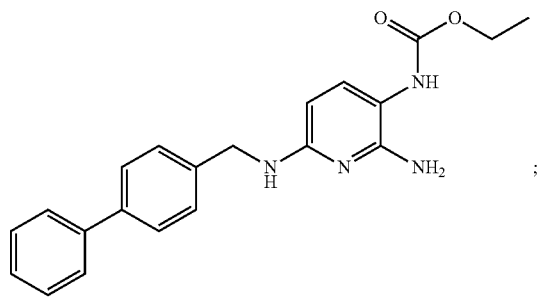 [SMILES: CCOC(=O)Nc1ccc(NCc2ccc(-c3ccccc3)cc2)nc1N] ; |
| NK-60-3 | 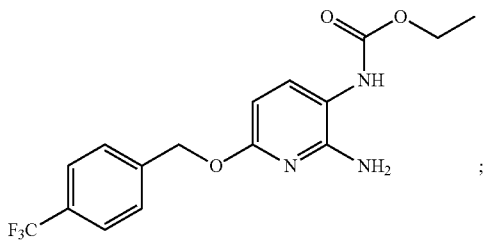 ; |
| NK-64-3 | 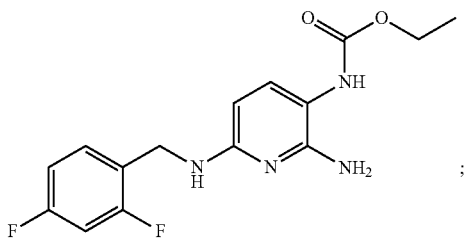 [SMILES: CCOC(=O)Nc1ccc(NCc2ccc(F)cc2F)nc1N] ; |
| NK-65-3 | 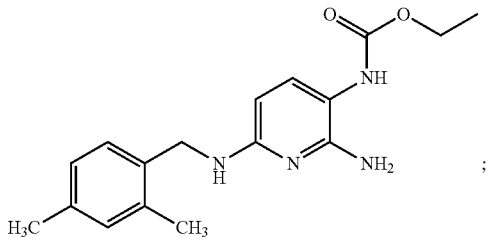 [SMILES: CCOC(=O)Nc1ccc(NCc2ccc(C)cc2C)nc1N] ; |

-continued
Table of Compounds:
NK-66-3
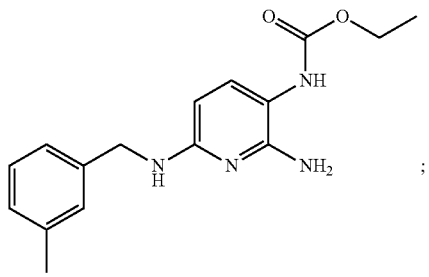 [SMILES: CCOC(=O)Nc1ccc(NCc2cccc(C)c2)nc1N]
;
NK-67-3
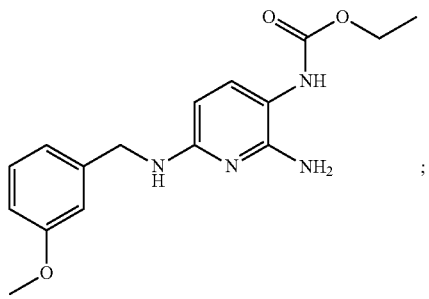 [SMILES: CCOC(=O)Nc1ccc(NCc2cccc(OC)c2)nc1N]
;
3G-4-5
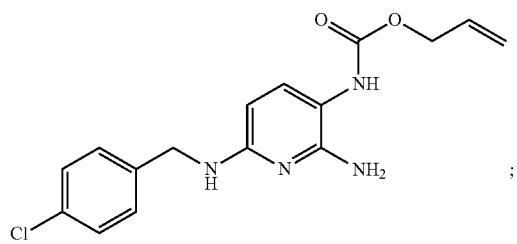 [SMILES: C=CCOC(=O)Nc1ccc(NCc2ccc(Cl)cc2)nc1N]
;
JG-32-3
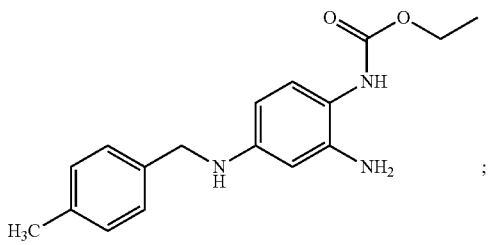 [SMILES: CCOC(=O)Nc1ccc(NCc2ccc(C)cc2)cc1N]
;
JG-33-4
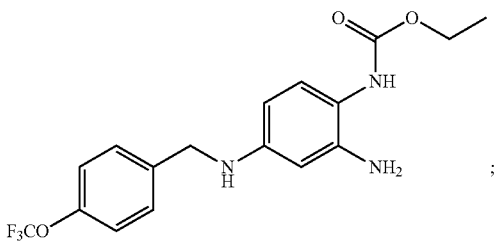
;
JG-34-4
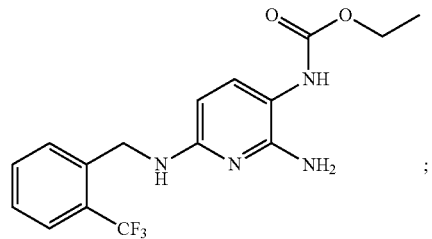 [SMILES: CCOC(=O)Nc1ccc(NCc2ccccc2C(F)(F)F)nc1N]
;

-continued
Table of Compounds:
JG-35-4
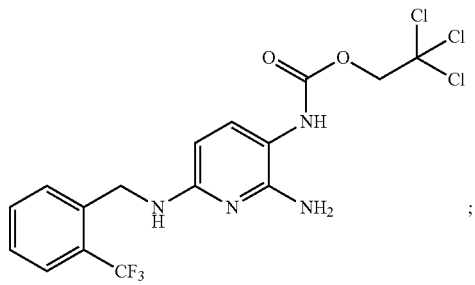 [SMILES: Nc1nc(NCc2ccccc2C(F)(F)F)ccc1NC(=O)OCC(Cl)(Cl)Cl]
JG-36-4
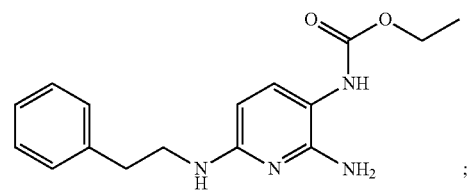 [SMILES: CCOC(=O)Nc1ccc(NCCc2ccccc2)nc1N]
JG-38-4
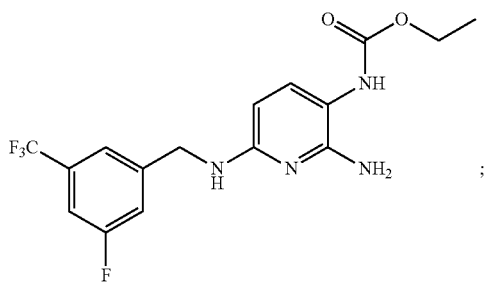 [SMILES: CCOC(=O)Nc1ccc(NCc2cc(F)cc(C(F)(F)F)c2)nc1N]
JG-41-4
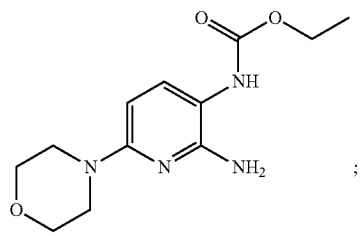 [SMILES: CCOC(=O)Nc1ccc(N2CCOCC2)nc1N]
JG-48-6
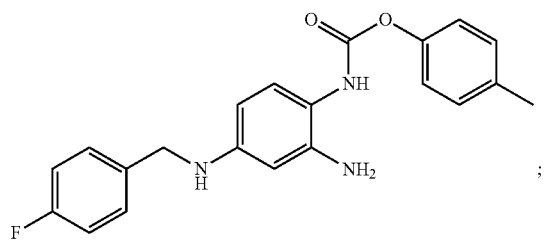 [SMILES: Cc1ccc(OC(=O)Nc2ccc(NCc3ccc(F)cc3)cc2N)cc1]
AM-2-3
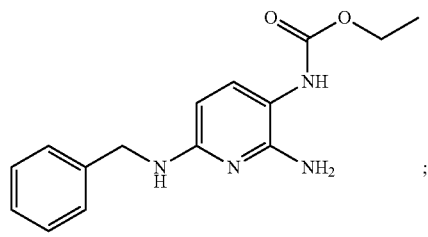 [SMILES: CCOC(=O)Nc1ccc(NCc2ccccc2)nc1N]

-continued
Table of Compounds:
AM-4-3
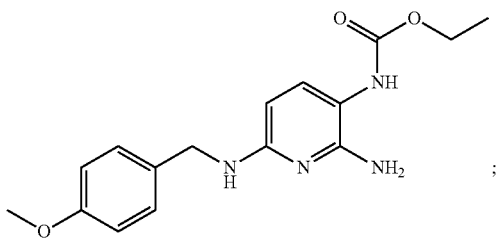 [SMILES: CCOC(=O)Nc1ccc(NCc2ccc(OC)cc2)nc1N]
;
AM-5-3
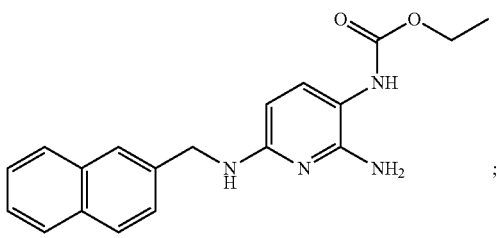 [SMILES: CCOC(=O)Nc1ccc(NCc2ccc3ccccc3c2)nc1N]
;
AM-8-3
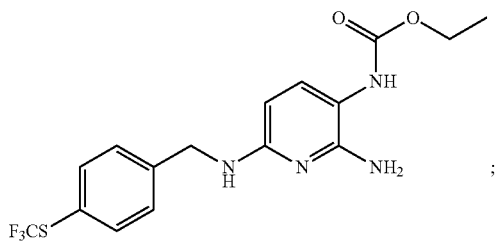
;
AM-11-3
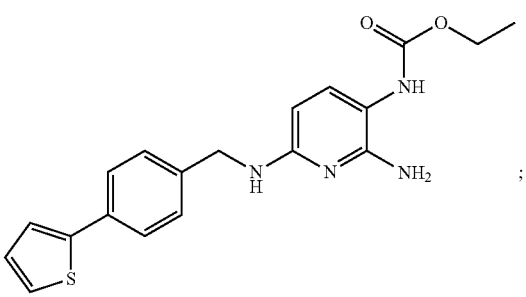
;
or
AM-15-3
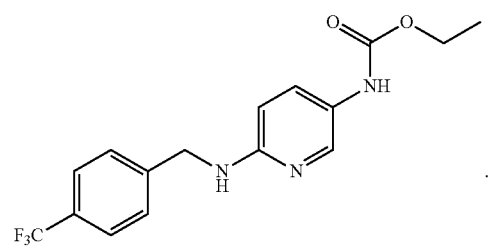 [SMILES: CCOC(=O)Nc1ccc(NCc2ccc(C(F)(F)F)cc2)nc1]
.
NK-48-3
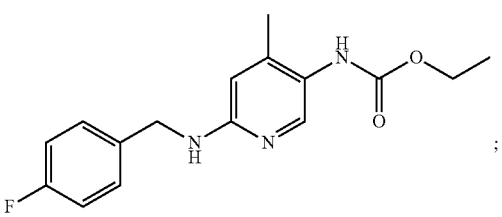 [SMILES: CCOC(=O)Nc1cnc(NCc2ccc(F)cc2)cc1C]
;

In one aspect, the method of claim 1, wherein the amount of the compound is effective to reduce a symptom of the neurodegenerative disorder or disease in the subject. In another aspect, the neurodegenerative disorder or disease is a brain atrophy, neuronal dysfunction, neuronal injury, neuronal degeneration, neuronal apoptosis, risk for confirmed progression, deterioration of visual function, fatigue, impaired mobility, cognitive impairment, or reduction of brain volume. In another aspect, the amount of compound is effective to reduce cognitive impairment. In another aspect, the method further comprises adapting the composition for oral, intravenous, cutaneous, peritoneal, parenteral, rectal, pulmonary, nasal, administration. In another aspect, the method further comprises adapting the composition for slow release form or an immediate release form. In another aspect, the method further comprises combining the composition with a pharmaceutically acceptable excipient. In another aspect, the method further comprises combining the composition with the pharmaceutically acceptable excipient that is selected from at least one of lactose, lactose monohydrate, starch, isomaltose, mannitol, sodium starch glycolate, sorbitol, lactose spray dried, lactose anhydrous, or a combination thereof. In another aspect, the method further comprises adapting the composition for administration daily, more often than once daily, or less often than once daily. In another aspect, the method further comprises adapting the composition for administration from 10-1000 mg/day. In another aspect, the method further comprises the composition for administration from 50-500 mg/day, or 100-400 mg/day.

In another embodiment, the present invention includes a composition comprising at least one compound selected from the Table of Compounds above.

In one aspect, the amount of the compound is formulated into a dosage form that is effective to reduce a symptom of the neurodegenerative disorder or disease in the subject. In another aspect, the neurodegenerative disorder or disease is a brain atrophy, neuronal dysfunction, neuronal injury, neuronal degeneration, neuronal apoptosis, risk for confirmed progression, deterioration of visual function, fatigue, impaired mobility, cognitive impairment, or reduction of brain volume. In another aspect, the composition is adapted for oral, intravenous, cutaneous, peritoneal, parenteral, rectal, pulmonary, nasal, administration. In another aspect, the composition is adapted for slow release form or an immediate release form. In another aspect, the composition further comprises a pharmaceutically acceptable excipient. In another aspect, the composition further comprises a pharmaceutically acceptable excipient selected from at least one of lactose, lactose monohydrate, starch, isomaltose, mannitol, sodium starch glycolate, sorbitol, lactose spray dried, lactose anhydrous, or a combination thereof. In another aspect, the composition is adapted for administration daily, more often than once daily, or less often than once daily. In another aspect, the composition is adapted for administration from 10-1000 mg/day. In another aspect, the composition is adapted for administration from 50-500 mg/day, or 100-400 mg/day.

In yet another embodiment, the present invention includes a pharmaceutical composition comprising at least one compound selected from Table of Compounds above.

In one aspect, the neurodegenerative disorder or disease is a brain atrophy, neuronal dysfunction, neuronal injury, neuronal degeneration, neuronal apoptosis, risk for confirmed progression, deterioration of visual function, fatigue, impaired mobility, cognitive impairment, or reduction of brain volume. In another aspect, the composition is adapted for oral, intravenous, cutaneous, peritoneal, parenteral, rectal, pulmonary, nasal, administration. In another aspect, the composition is adapted for slow release form or an immediate release form. In another aspect, the composition further comprises a pharmaceutically acceptable excipient. In another aspect, the composition further comprises a pharmaceutically acceptable excipient selected from at least one of lactose, lactose monohydrate, starch, isomaltose, mannitol, sodium starch glycolate, sorbitol, lactose spray dried, lactose anhydrous, or a combination thereof. In another aspect, the composition is adapted for administration daily, more often than once daily, or less often than once daily. In another aspect, the composition is adapted for administration from 10-1000 mg/day. In another aspect, the composition is adapted for administration from 50-500 mg/day, or 100-400 mg/day.

DESCRIPTION OF THE DRAWINGS

For a more complete understanding of the features and advantages of the present invention, reference is now made to the detailed description of the invention along with the accompanying figures and in which:

FIGS. 3A and 3B show the neuroprotective effect of selected compounds in phenotypic cell lines. In FIG. 3A, the protective effect is shown in siRNA CLN3 knock down PC12 cells. In FIG. 3B the protective effect is shown in wild-type (WT) and CLN3 knock down mouse fibroblasts. Values are represented as mean±SD. *$P<0.05$, $p<0.01$, *$p<0.001$ compared to vehicle control, unpaired student t test.

FIGS. 4A to 4E show the percentage of patient lymphoblast cells (%), using Trypan Blue dye with Flupirtine (20 μM, vehicle %1 EtOH), drug 3 (20 μM, vehicle %1 EtOH), drug 5 (50 μM, vehicle %4 DMSO) or drug 6 (20 μM, vehicle %4 DMSO) at 24 h. CLN1 (FIG. 4A), CLN2 (FIG. 4B), CLN3 (FIG. 4C), CLN6 (FIG. 4D), and CLN8 (FIG. 4E).

FIG. 5A shows the hit compounds flupirtine (1) and retigabine (2) demonstrate antioxidant activity. However, equipotent or greater potency protective derivatives (3 and 4) do not act as antioxidants. PC12 cells stained with CellROX and DAPI-blue nuclear stain. Greater intensity of green fluorescence indicates greater levels of ROS. Visualized through a microscope (40× magnification, bar=100 μM). FIG. 5B shows fluorescence measured using prestoblue dye after treating PC12 cells with respective molecules.

DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The drug flupirtine, and its bioisostere retigabine, have both shown to be potentially promising drugs for the treatment of neurodegenerative diseases; retigabine has just entered phase II clinical trials as a treatment for the neurodegenerative disease Amyotrophic Lateral Sclerosis (ALS). While the drugs are widely known to be neuroprotective, their exact mechanisms of neuroprotection in certain diseased cells have not yet been fully elucidated. Additionally, regarding flupirtine, it has been reported that neuroprotective activity in vitro can only be achieved at concentrations higher than 20 μM, a concentration difficult to achieve and maintain in vivo. As such, more potent compounds could provide significant in vivo effects.

The disclosed technology encompasses multiple derivatives of both flupirtine and retigabine. One of these derivatives (NK-40-3) has been shown to have neuroprotective activity at a concentration as low as 0.1 μM in human IMR-90-derived neurons. Other derivatives, while not as potent as NK-40-3, have shown to be more potent than both flupirtine and retigabine. The inventors provide further insight into the derivatives from both original molecules. Both flupirtine and retigabine are known antioxidants, but their derivatives disclosed here are not; they also do not function as NMDA antagonists. By way of explanation, and in no way a limitation of the present invention, the inventors have shown that the derivatives are active in two ways: they (1) upregulate expression of the anti-apoptotic protein Bcl-2 and ceramide pathway synthesis enzymes, and (2) activate autophagy. Both of these mechanisms work to suppress cell death, suggesting a unique multi-modal mechanism of action.

Figure 1:
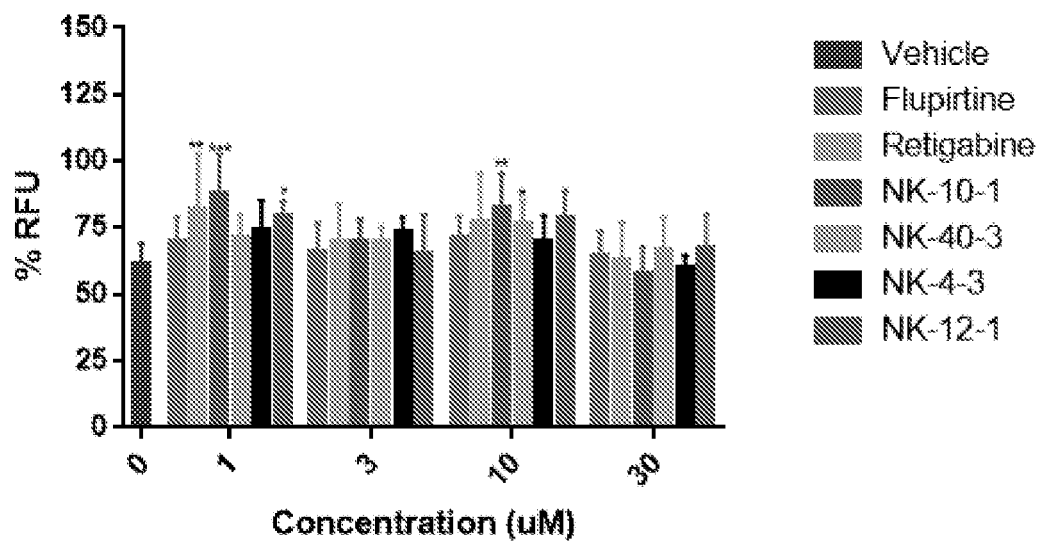
FIG. 1 is a graph that shoes that flupirtine analogues are protective against etoposide-induced apoptosis in human SH-SY5Y cells. RFU measured using prestoblue dye after treatment with μM etoposide for hours. Two-Way ANOVA, Tukey Test, 95% Confidence Interval. *-$p<0.05$, -$p<0.01$, *-$p<0.001$, ****-$p<0.0001$.
Figure 2:
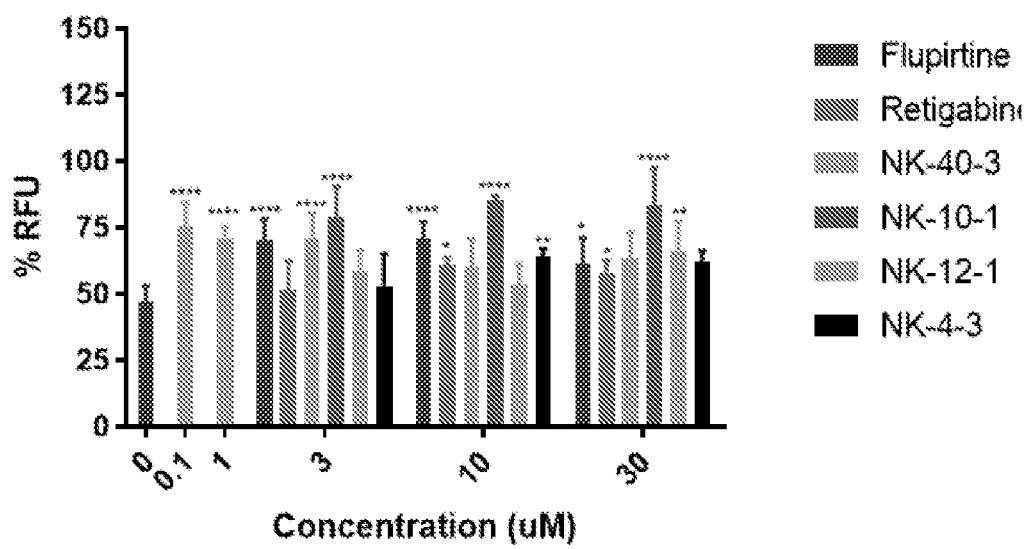
FIG. 2 is a graph that compares flupirtine analogues ameliorate against etoposide-induced apoptosis in neurons differentiated from IMR-90. RFU measured using prestoblue dye after treatment with 15 ug/mL etoposide for 36 hours. Two-Way ANOVA, Tukey Test, 95% Confidence Interval. *-$p<0.05$, -$p<0.01$, *-$p<0.001$, ****-$p<0.0001$.

The present inventors have designed and synthesized a wide range of flupirtine and retigabine derivatives and determined their effect to ameliorate etoposide-induced apoptosis in neuron-like PC12 cells. The results from cell viability determination in neuron-like PC12 cells have provided a preliminary SAR (Table 1) that translates to phenotypic cell lines (FIG. 1) and allows the rational design of further analogues with MPO scores favorable for brain penetration (Table 2). The majority of compounds were found to provide the most effective protection of cell viability at 3 μM. As this is an obtainable in vivo concentration the present invention can be used at concentrations of 3 μM to compare the protective ability of the compound library. Selected compounds were also assayed in a secondary screen to determine their effect to ameliorate serum starvation-induced apoptosis in neuron-like PC12 cells. Results from this assay follow the same trend as seen in the etoposide-induced apoptosis assay; those compounds that are protective in the etoposide-based assay are protective in the serum starvation based assay (Table 2). This data shows that the compounds do not simply act to block the action of etoposide and do elicit a protective effect. Table 3 shows the predicted MPO Score (brain penetration) for the various compounds. FIG. 1 is a graph that shoes that flupirtine analogues are protective against etoposide-induced apoptosis in human SH-SY5Y cells. RFU measured using prestoblue dye after treatment with μM etoposide for hours. Two-Way ANOVA, Tukey Test, 95% Confidence Interval. *-$p<0.05$, -$p<0.01$, *-$p<0.001$, ****-$p<0.0001$. FIG. 2 is a graph that compares flupirtine analogues ameliorate against etoposide-induced apoptosis in neurons differentiated from IMR-90. RFU measured using prestoblue dye after treatment with 15 ug/mL etoposide for 36 hours. Two-Way ANOVA, Tukey Test, 95% Confidence Interval. *-$p<0.05$, -$p<0.01$, *-$p<0.001$, ****-$p<0.0001$.

In certain aspect, the most potent compound yet identified, derivative NK-40-3, containing the electron-withdrawing group (EWG) $CF_3$, provides protection of PC12 cells from etoposide-induced cell death at a concentration of just 0.1 μM. Addition of the same EWG to the 3-position (compound NK-16-6) also provides greater activity, suggesting a general trend of this group to enhance activity. Switching an EWG fluorine for an electron-donating methyl group (compound JG-32-3) also provides a significant increase in potency. Derivative NK-31-3 suggests that the amine moiety is not required for protective activity.

Given these observations the present invention can be used to target further analogues of the benzylamine ring and amine excised analogues to further enhance the protective effect of this class of compound. Cell viability values of >100% suggest that these compounds may play a role in triggering proliferation or neurogenesis. Enhanced expression of anti-apoptotic proteins, including Bcl-2, are known to enhance neurogenesis in adult mice. Such compounds will be screened in CLN3 siRNA knock down PC12 cells, human CLN3 deficient lymphoblasts and JNCL iPSC-derived neurons to confirm these observations in a phenotypic screen. If >100% viability is detected in these cell lines the use of 'CellTrace' dye with flow cytometry will be employed to determine extent of cell division verses cell viability.

Protective Effect in Phenotypic Cell Lines. The present inventors validated the use of PC12 cells as an initial assay to identify neuroprotective compounds and exclude toxic compounds by confirming translation of neuroprotective activity to phenotypic cells lines. The inventors screened a number of compounds in both neuron-like CLN3 siRNA knock down PC12 cells (FIG. 3A) and CLN3 knockdown mouse fibroblasts (FIG. 3B) as phenotypic models of JNCL. Flupirtine demonstrates protective activity in both phenotypic assays. FIGS. 3A and 3B show the neuroprotective effect of selected compounds in phenotypic cell lines. In FIG. 3A, the protective effect is shown in siRNA CLN3 knock down PC12 cells. In FIG. 3B the protective effect is shown in wild-type (WT) and CLN3 knock down mouse fibroblasts. Values are represented as mean±SD. *P<0.05, p<0.01, *p<0.001 compared to vehicle control, unpaired student t test. Flupirtine analogues NK-10-1 (benzyl carbamate) and NK-12-1 (allyl carbamate), which show greater neuroprotective activity in the WT PC12 cell assay also show greater activity than flupirtine in the two phenotypic assays. Compound NK-4-3, is less active than compounds NK-10-1 and NK-12-1 in the WT PC12 assay and less active in the iPSC-derived neurons, further justifying the value of the initial WT PC12 assay. Selected derivatives show greater protective effect than flupirtine in patient lymphoblast cells in CLN1, CLN2, CLN3, CLN6 and CLN8 disease (FIGS. 4A to 4E). FIGS. 4A to 4E show the percentage of patient lymphoblast cells (%), using Trypan Blue dye with Flupirtine (20 µM, vehicle %1 EtOH), drug 3 (20 µM, vehicle %1 EtOH), drug 5 (50 µM, vehicle %4 DMSO) or drug 6 (20 µM, vehicle %4 DMSO) at 24 h. CLN1 (FIG. 4A), CLN2 (FIG. 4B), CLN3 (FIG. 4C), CLN6 (FIG. 4D), and CLN8 (FIG. 4E).

Figure 5A:
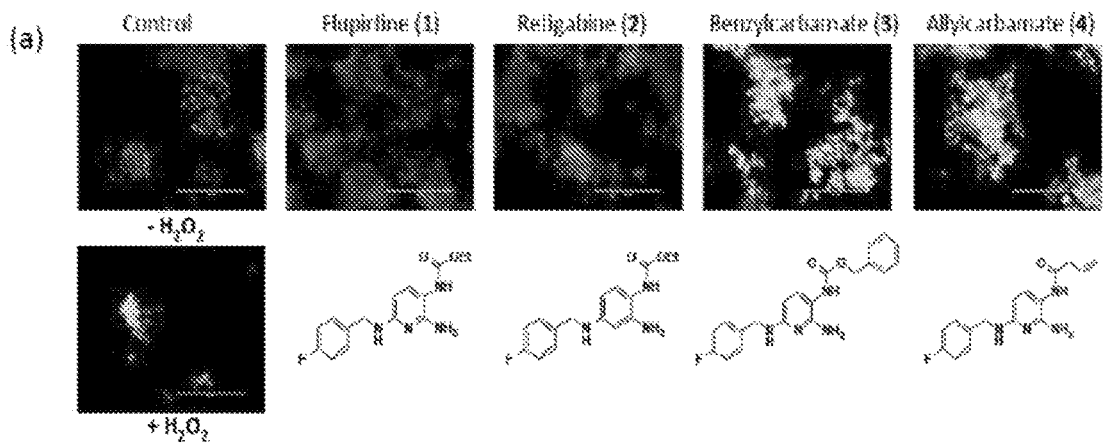
FIGS. 5A and 5B show flupirtine analogues do not act as antioxidants when treated with 400 μM $H_2O_2$ for 4 hours.
Figure 5B:
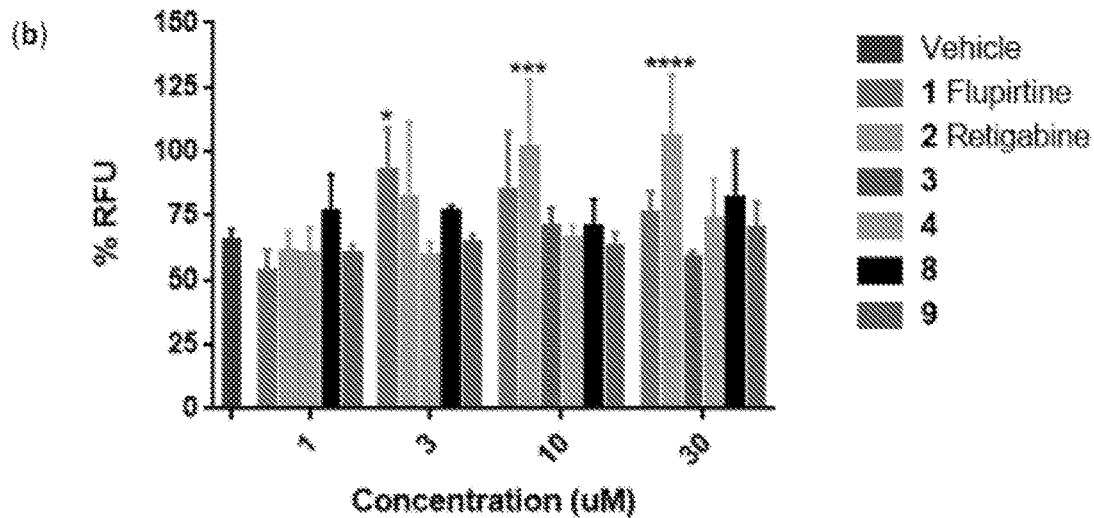

Neuroprotective derivatives do not function as antioxidants. While flupirtine and retigabine are known antioxidants the inventors have shown (FIGS. 5A and 5B) that neuroprotective derivatives operate by a different mechanism of action. Exposure of PC12 cells to flupirtine, retigabine, NK-10-1 (benzyl carbamate) and NK-12-1 (allyl carbamate) and staining with CellROX green dye and DAPI blue nuclear stain indicate no amelioration of reactive oxygen species (ROS) upon treatment with neuroprotective derivatives NK-10-1 (benzyl carbamate) and NK-12-1 (allyl carbamate) while retigabine and flupirtine do ameliorate ROS (FIG. 5A). Neuroprotective derivatives do not provide protective effect to amerliorate $H_2O_2$-induced cell death in PC12 cells providing further evidence that antioxidant effect is not a mechanism of action of protective derivatives (FIG. 5B). FIGS. 5A and 5B show flupirtine analogues do not act as antioxidants when treated with 400 µM $H_2O_2$ for 4 hours. FIG. 5A shows the hit compounds flupirtine (1) and retigabine (2) demonstrate antioxidant activity. However, equipotent or greater potency protective derivatives (3 and 4) do not act as antioxidants. PC12 cells stained with CellROX and DAPI-blue nuclear stain. Greater intensity of green fluorescence indicates greater levels of ROS. Visualized through a microscope (40× magnification, bar=100 µM). FIG. 5B shows fluorescence measured using prestoblue dye after treating PC12 cells with respective molecules.

Figure 6:
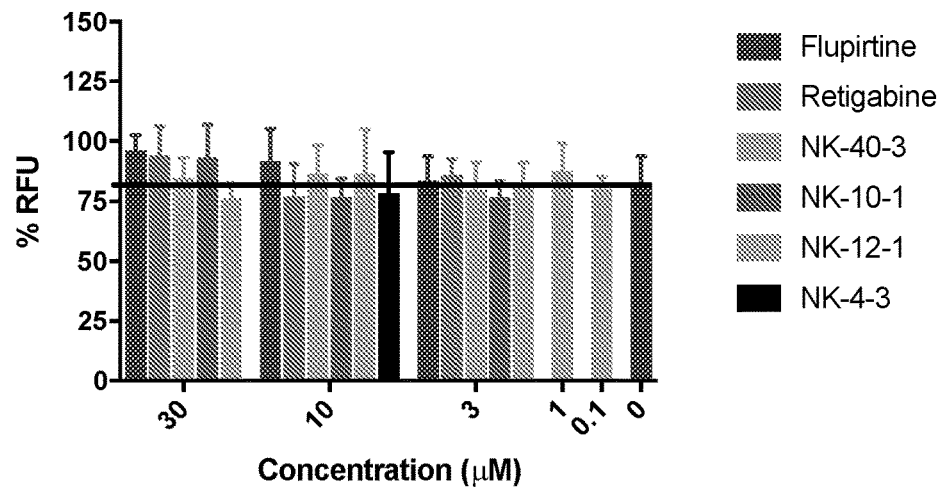
FIG. 6 is a graph that shows the efficacy of flupirtine analogues in iPSC IMR90-derived neurons. Cells were pretreated with flupirtine analogues for 4 hours and 500 μM NMDA was added and incubated for 36 hours. RFU was measured using prestoblue after incubation for 1 hour.

Neuroprotective derivatives do not function as NMDA antagonists. A selection of protective derivatives where exposed to human IMR-90-derived neurons for 4 hours and then a toxic quantity of N-methyl-D-aspartate (NMDA) introduced (FIG. 6). None of the protective derivatives showed activity to ameliorate NMDA-induced toxicity suggestion that this class of compound does not function at the NMDA receptor. FIG. 6 is a graph that shows the efficacy of flupirtine analogues in iPSC IMR90-derived neurons. Cells were pretreated with flupirtine analogues for 4 hours and 500 µM NMDA was added and incubated for 36 hours. RFU was measured using prestoblue after incubation for 1 hour.

Figure 7A:
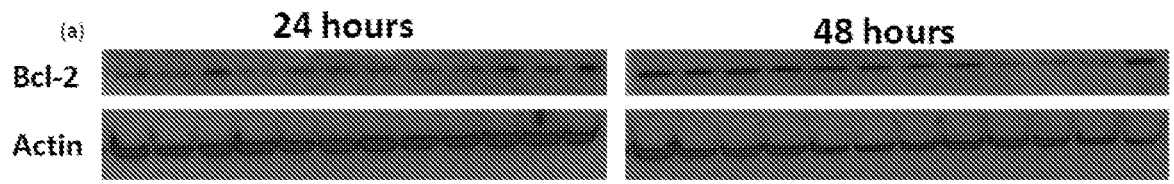
FIG. 7A shows the effect on Bcl-2 levels measured using western blot after treatment with flupirtine analogues after treatment with 15 μg/mL etoposide.
Figure 7B:
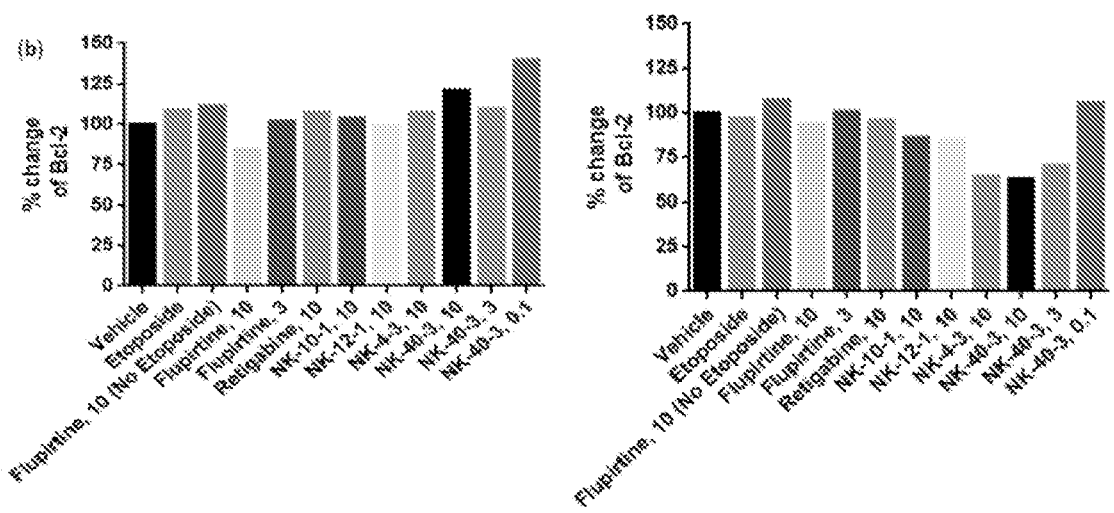
FIG. 7B shows graphs that quantified the results of the western blot. A transient increase in Bcl-2 levels was observed at 24 hours, which started to decline at 48 hours.
Figure 8:
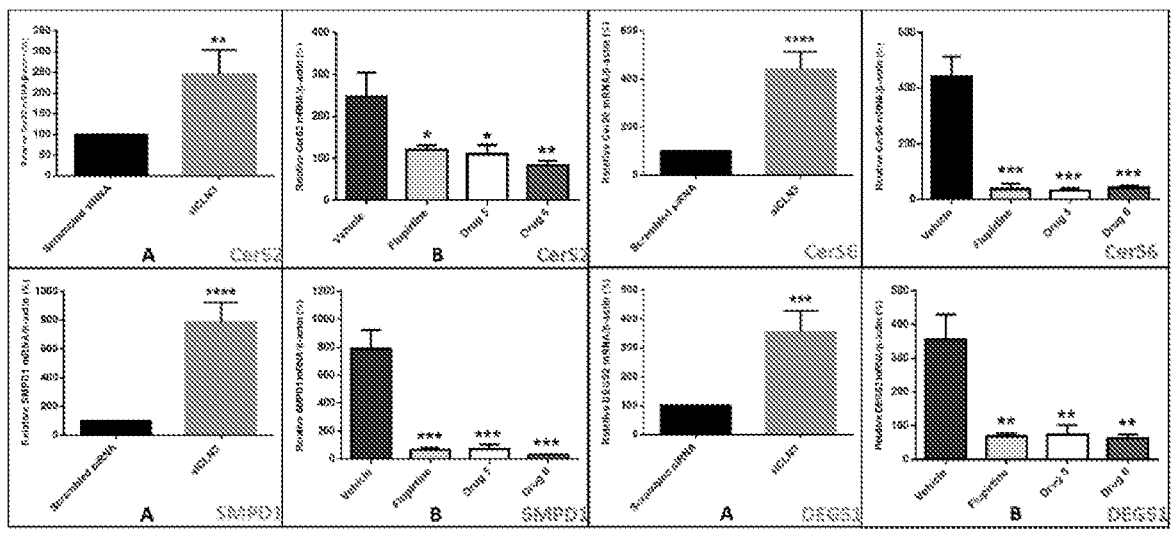
FIG. 8 includes side-by-side graphs that compare relative ceramide pathway synthesis enzymes mRNA/β-actin (%) of PC12 transfected cells with siCLN3 compared to scrambled siRNA (A) and transfected PC12 with Flupirtine (20 μM vehicle %1 EtOH), drug 3 (20 μM, vehicle %1 EtOH), drug 5 (50 μM, vehicle %4 DMSO) or drug 6 (20 μM, vehicle %4 DMSO) at 24 h (B).

Neuroprotective derivatives upregulate expression of the anti-apoptotic protein Bcl-2 and ceramide pathway synthesis enzymes. One mechanism of survival for neurons in JNCL is upregulation of the apoptotic regulator protein Bcl-2. Likewise, the CLN3 gene, mutated in the disease state, is known to exhibit anti-apoptotic properties, exerting this effect by upregulation of the same protein. This effect may also counter SOD1-induced damage in amyotrophic lateral sclerosis. The inventors show by Western blot analysis that selected neuroprotective derivatives transiently upregulate the expression of Bcl-2 over a 24 hour period (FIGS. 7A and 7B). Compounds also have an effect to reduce ceramide pathway synthesis enzymes (FIG. 8). Ceramide is recognized as a critical messenger playing an essential roles to regulate cell growth, survival and death. FIG. 7A shows the effect on Bcl-2 levels measured using western blot after treatment with flupirtine analogues after treatment with 15 µg/mL etoposide. FIG. 7B shows graphs that quantified the results of the western blot. A transient increase in Bcl-2 levels was observed at 24 hours, which started to decline at 48 hours. FIG. 8 includes side-by-side graphs that compare relative ceramide pathway synthesis enzymes mRNA/β-actin (%) of PC12 transfected cells with siCLN3 compared to scrambled siRNA (A) and transfected PC12 with Flupirtine (20 µM vehicle %1 EtOH), drug 3 (20 µM, vehicle %1 EtOH), drug 5 (50 µM, vehicle %4 DMSO) or drug 6 (20 µM, vehicle %4 DMSO) at 24 h (B).

Figure 9:
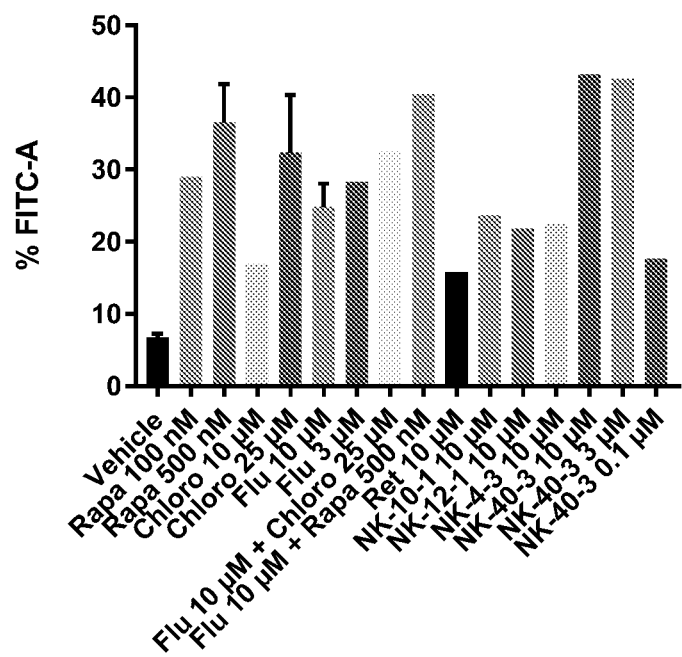
FIG. 9 is a graph of the effect of flupirtine analogues on autophagy measured using monodansylcadaverine staining by flow cytometry after 48 hours of treatment. All analogues increase the FITC staining, indicating a modulation in autophagy.

Neuroprotective derivatives activate autophagy: Autophagy is essential for neuronal homeostasis and its dysfunction has been directly linked to a growing number of neurodegenerative disorders. Abnormal accumulation of undigested macromolecules in both autophagosomes and lysosomes is phenotypic of the NCLs and is attributed to defective autophagy. As autophagy dysfunction is an early indication of CLN3 disease and therefore has potential to rescue neurons before death. Neuroprotective derivatives that show protective effect in IMR-90-derived neurons substantially activate autophagy after 48 hr treatment (FIG. 9). FIG. 9 is a graph of the effect of flupirtine analogues on autophagy measured using monodansylcadaverine staining by flow cytometry after 48 hours of treatment. All analogues increase the FITC staining, indicating a modulation in autophagy.

In summary, the present inventors have developed compounds that exert a protective effect to suppress cell death in both human iPSC-derived neurons and phenotypic cell lines for CLN3 disease. These compounds function to both enhance Bcl-2 expression and increase autophagy in a concentration dependent manner TABLE 1
Protective effect of flupirtine derivatives to ameliorate etoposide-induced apoptosis in PC12 cells.
| Code | Structure | % Viability- 0.1 μM | % Viability- 0.3 μM | % Viability 1 μM | % Viability 3 μM | % Viability 10 μM | % Viability 30 μM |
|---|---|---|---|---|---|---|---|
| Vehicle | | 52.1 ± 7.32 | | | | | |
| NK-1-4 (Flu) | 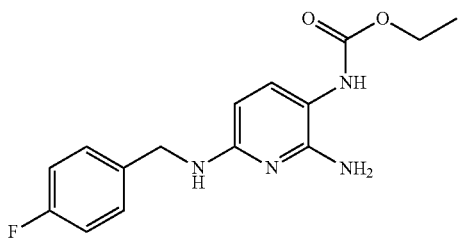 [SMILES: CCOC(=O)Nc1ccc(NCc2ccc(F)cc2)nc1N] | 67.02 ± 5.88 | 64.36 ± 9.35 | 73.18 ± 13.94 | 78.09 ± 12.93 | 76.88 ± 17.35 | 71.32 ± 18.01 |
| NK-3-1 | 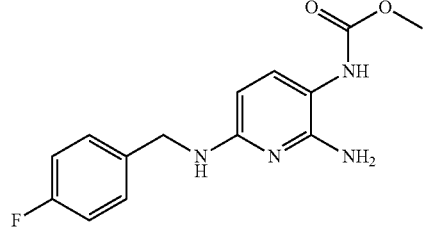 | | | 74.50 ± 33.12 | 96.64 ± 14.62 | 82.19 ± 23.39 | 63.31 ± 27.40 |
| NK-4-3 | 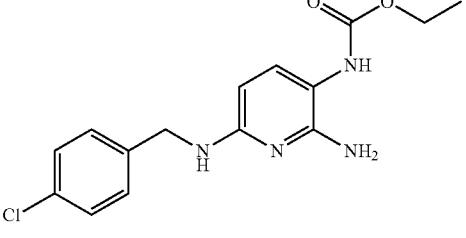 | | | 65.71 ± 16.16 | 64.32 ± 4.28 | 52.58 ± 10.29 | 41.53 ± 6.14 |
| NK-8-1 | 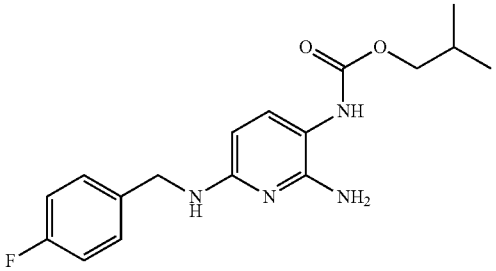 [SMILES: CC(C)COC(=O)Nc1ccc(NCc2ccc(F)cc2)nc1N] | | | 57.88 ± 22.44 | 62.91 ± 2.98 | 46.48 ± 3.36 | 56.15 ± 0.67 |
| NK-10-1 | 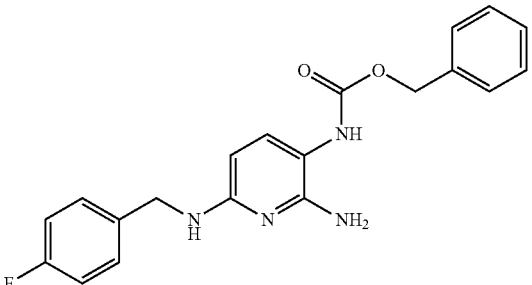 | | | 60.07 ± 7.91 | 82.05 ± 4.43 | 66.24 ± 6.26 | 57.44 ± 2.24 |

TABLE 1-continued

Protective effect of flupirtine derivatives to ameliorate etoposide-induced apoptosis in PC12 cells.

| Code | Structure | % Viability- 0.1 μM | % Viability- 0.3 μM | % Viability 1 μM | % Viability 3 μM | % Viability 10 μM | % Viability 30 μM |
|---|---|---|---|---|---|---|---|
| NK-12-1 | 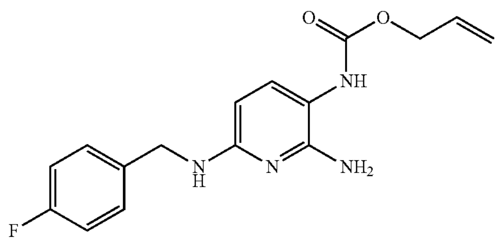 [SMILES: C=CCOC(=O)Nc1ccc(NCc2ccc(F)cc2)nc1N] | | | 65.47 ± 8.19 | 86.75 ± 9.05 | 67.48 ± 22.63 | 45.22 ± 8.92 |
| NK-13-1 | 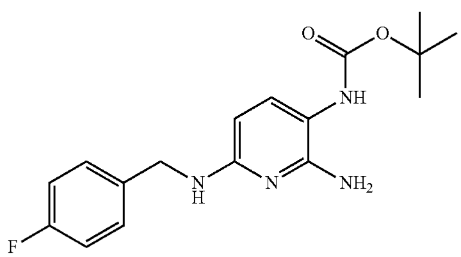 [SMILES: CC(C)(C)OC(=O)Nc1ccc(NCc2ccc(F)cc2)nc1N] | 53.47 ± 9.17 | 47.64 ± 3.19 | 57.23 ± 13.63 | 42.17 ± 6.03 | 68.10 ± 21.60 | 64.38 ± 12.85 |
| NK-16-3 | 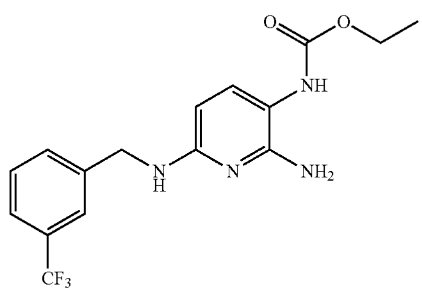 [SMILES: CCOC(=O)Nc1ccc(NCc2cccc(C(F)(F)F)c2)nc1N] | | | 59.89 ± 13.77 | 68.17 ± 7.50 | 60.40 ± 19.40 | 46.43 ± 12.82 |
| NK-16-4 | 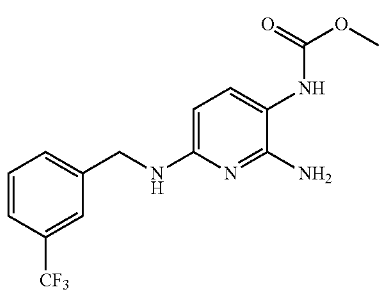 [SMILES: COC(=O)Nc1ccc(NCc2cccc(C(F)(F)F)c2)nc1N] | | | 46.71 ± 3.26 | 41.28 ± 10.11 | 28.56 ± 2.14 | 37.01 ± 3.91 |
| NK-16-6 | 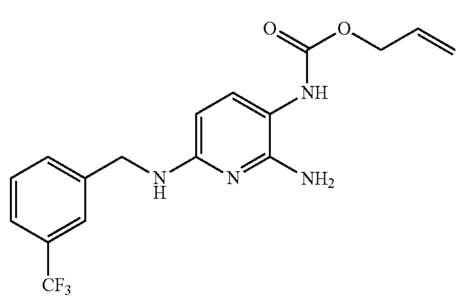 [SMILES: C=CCOC(=O)Nc1ccc(NCc2cccc(C(F)(F)F)c2)nc1N] | | | 78.05 ± 37.07 | 107.25 ± 2.3 | 100.70 ± 9.58 | 87.58 ± 21.89 |

TABLE 1-continued

Protective effect of flupirtine derivatives to ameliorate etoposide-induced apoptosis in PC12 cells.

| Code | Structure | % Viability- 0.1 µM | % Viability- 0.3 µM | % Viability 1 µM | % Viability 3 µM | % Viability 10 µM | % Viability 30 µM |
|---|---|---|---|---|---|---|---|
| NK-17-3 | 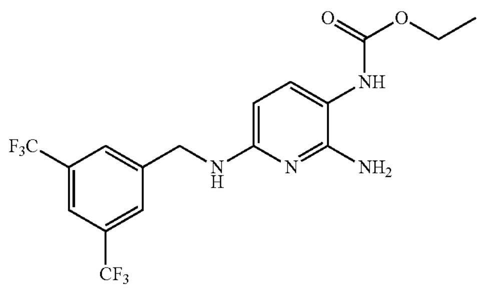 [SMILES: CCOC(=O)Nc1ccc(NCc2cc(C(F)(F)F)cc(C(F)(F)F)c2)nc1N] | | | 63.74 ± 22.66 | 75.70 ± 6.39 | 68.11 ± 9.52 | 56.00 ± 6.26 |
| NK-21-1 | 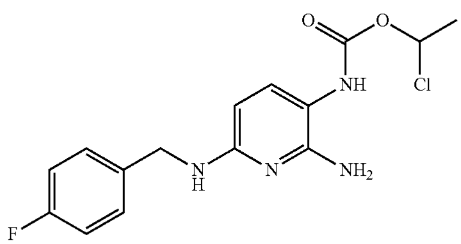 [SMILES: CC(Cl)OC(=O)Nc1ccc(NCc2ccc(F)cc2)nc1N] | | | 69.51 ± 13.17 | 88.94 ± 21.49 | 84.31 ± 32.19 | 84.80 ± 33.67 |
| NK-22-6 | 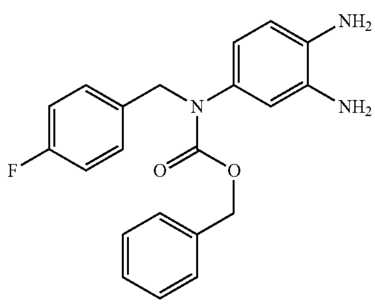 [SMILES: Nc1ccc(N(Cc2ccc(F)cc2)C(=O)OCc2ccccc2)cc1N] | | | 69.07 ± 20.11 | 100.27 ± 5.4 | 98.91 ± 7.93 | 78.61 ± 22.99 |
| NK-22-13 (Ret) | 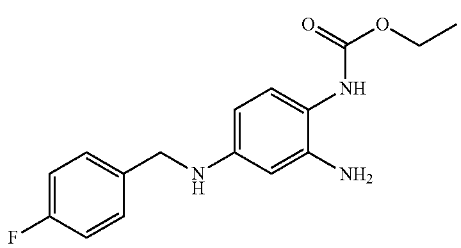 [SMILES: CCOC(=O)Nc1ccc(NCc2ccc(F)cc2)cc1N] | | | 58.34 ± 2.86 | 73.92 ± 13.90 | 66.26 ± 17.56 | 52.11 ± 7.62 |
| NK-23-1 | 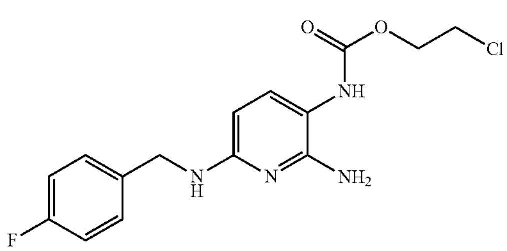 [SMILES: Nc1nc(NCc2ccc(F)cc2)ccc1NC(=O)OCCCl] | | | 54.01 ± 13.43 | 53.92 ± 6.37 | 41.79 ± 4.38 | 40.77 ± 6.98 |

TABLE 1-continued

Protective effect of flupirtine derivatives to ameliorate etoposide-induced apoptosis in PC12 cells.

| Code | Structure | % Viability- 0.1 μM | % Viability- 0.3 μM | % Viability 1 μM | % Viability 3 μM | % Viability 10 μM | % Viability 30 μM |
| --- | --- | --- | --- | --- | --- | --- | --- |
| NK-30-2 | 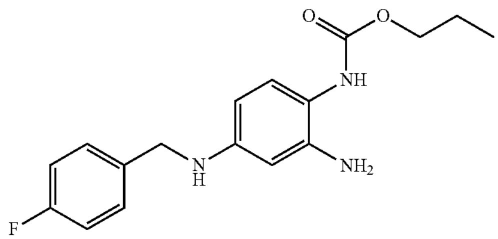 [SMILES: CCCOC(=O)Nc1ccc(NCc2ccc(F)cc2)cc1N] | | | 54.07 ± 9.34 | 55.56 ± 7.41 | 61.58 ± 4.82 | 61.64 ± 18.08 |
| NK-31-3 | 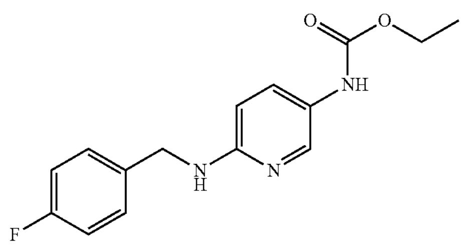 [SMILES: CCOC(=O)Nc1ccc(NCc2ccc(F)cc2)nc1] | | | 108.85 ± 35.88 | 109.51 ± 19.35 | 101.31 ± 15.91 | 69.34 ± 14.93 |
| NK-34-2 | 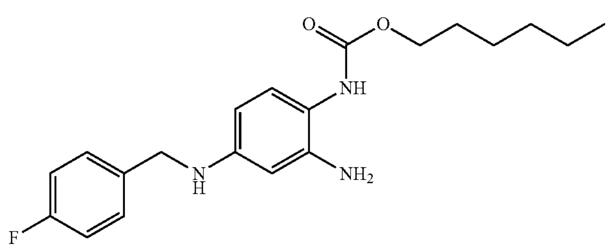 [SMILES: CCCCCCOC(=O)Nc1ccc(NCc2ccc(F)cc2)cc1N] | 63.03 ± 11.77 | 61.04 ± 5.70 | 65.75 ± 6.14 | 60.13 ± 11.41 | 72.10 ± 13.39 | 73.21 ± 4.74 |
| NK-40-3 | 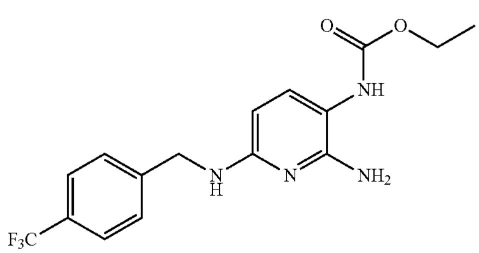 [SMILES: CCOC(=O)Nc1ccc(NCc2ccc(C(F)(F)F)cc2)nc1N] | 85.77 ± 11.82 | 108.84 ± 17.31 | 82.74 ± 8.82 | 71.50 ± 4.99 | 97.33 ± 22.75 | 105.79 ± 15.78 |
| NK-41-1 | 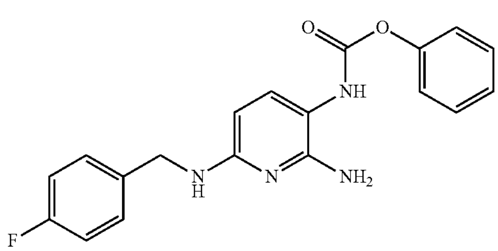 [SMILES: Nc1nc(NCc2ccc(F)cc2)ccc1NC(=O)Oc1ccccc1] | 57.45 ± 3.62 | 53.35 ± 0.80 | 58.13 ± 2.08 | 58.98 ± 6.87 | 68.90 ± 7.71 | 70.27 ± 10.61 |

TABLE 1-continued

Protective effect of flupirtine derivatives to ameliorate etoposide-induced apoptosis in PC12 cells.

| Code | Structure | % Viability- 0.1 μM | % Viability- 0.3 μM | % Viability 1 μM | % Viability 3 μM | % Viability 10 μM | % Viability 30 μM |
| --- | --- | --- | --- | --- | --- | --- | --- |
| NK-42-1 | 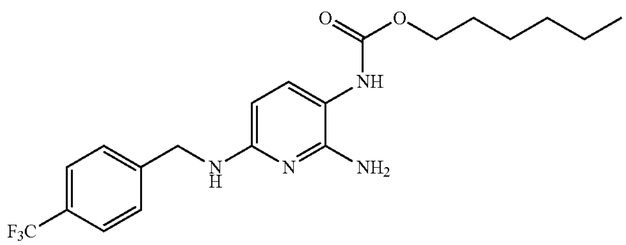 [SMILES: CCCCCCOC(=O)Nc1ccc(NCc2ccc(C(F)(F)F)cc2)nc1N] | 60.08 ± 3.34 | 59.19 ± 4.95 | 87.30 ± 18.26 | 78.46 ± 11.29 | 85.14 ± 11.29 | 78.95 ± 13.17 |
| NK-43-1 | 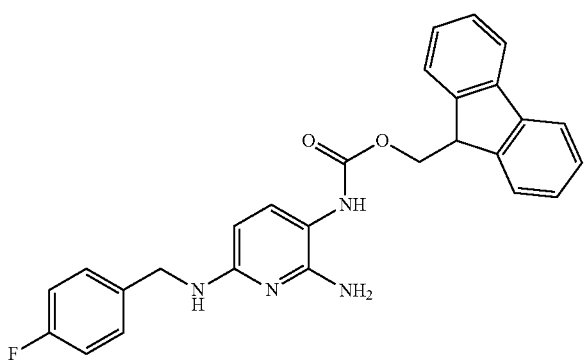 [SMILES: Nc1nc(NCc2ccc(F)cc2)ccc1NC(=O)OCC1c2ccccc2-c2ccccc21] | 67.45 ± 6.34 | 63.90 ± 6.20 | 68.95 ± 10.35 | 56.42 ± 8.99 | 66.72 ± 5.97 | 49.73 ± 1.76 |
| NK-45-1 | 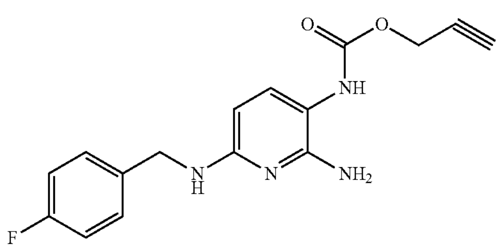 [SMILES: C#CCOC(=O)Nc1ccc(NCc2ccc(F)cc2)nc1N] | 60.39 ± 1.29 | 57.55 ± 3.95 | 64.91 ± 11.65 | 61.87 ± 9.82 | 65.37 ± 10.70 | 64.84 ± 3.90 |
| NK-46-1 | 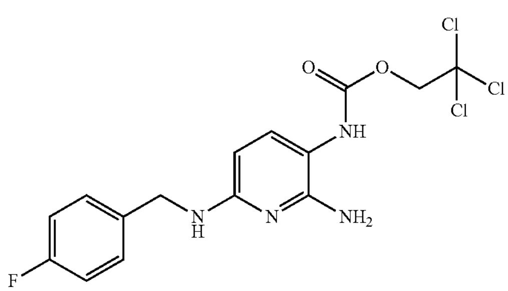 [SMILES: Nc1nc(NCc2ccc(F)cc2)ccc1NC(=O)OCC(Cl)(Cl)Cl] | 74.13 ± 9.21 | 107.83 ± 12.69 | 94.94 ± 8.18 | 77.25 ± 8.19 | 83.90 ± 18.00 | 113.32 ± 3.53 |
| NK-48-3 | 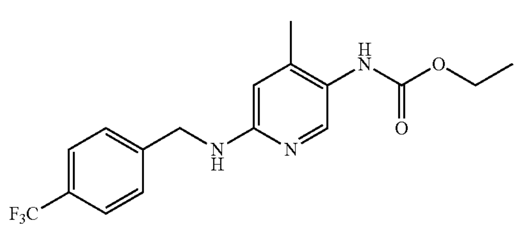 [SMILES: CCOC(=O)Nc1cnc(NCc2ccc(C(F)(F)F)cc2)cc1C] | 54.78 ± 2.77 | 57.46 ± 4.02 | 57.03 ± 1.81 | 53.80 ± 1.98 | 57.06 ± 4.28 | 63.25 ± 3.32 |

TABLE 1-continued

Protective effect of flupirtine derivatives to ameliorate etoposide-induced apoptosis in PC12 cells.

| Code | Structure | % Viability- 0.1 μM | % Viability- 0.3 μM | % Viability 1 μM | % Viability 3 μM | % Viability 10 μM | % Viability 30 μM |
|---|---|---|---|---|---|---|---|
| NK-52-3 | 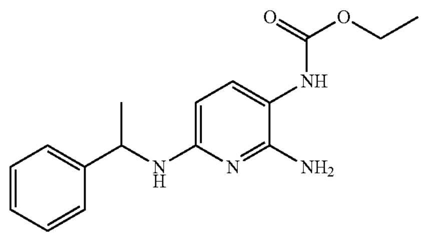 [SMILES: CCOC(=O)Nc1ccc(NC(C)c2ccccc2)nc1N] | 50.05 ± 1.04 | 55.98 ± 4.21 | 56.70 ± 5.69 | 66.17 ± 4.77 | 53.17 ± 2.30 | 23.98 ± 6.78 |
| NK-57-3 | 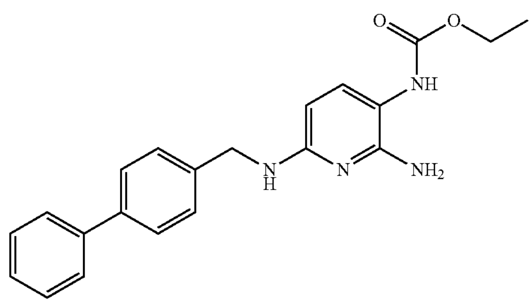 [SMILES: CCOC(=O)Nc1ccc(NCc2ccc(-c3ccccc3)cc2)nc1N] | 55.35 ± 14.83 | 61.67 ± 12.65 | 63.74 ± 10.08 | 48.88 ± 9.58 | 53.09 ± 13.99 | 62.28 ± 10.29 |
| NK-60-3 | 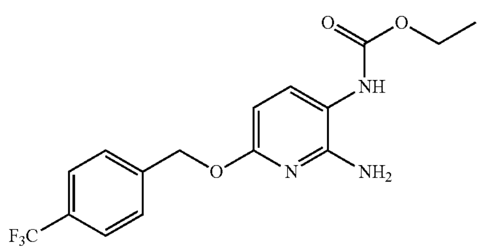 [SMILES: CCOC(=O)Nc1ccc(OCc2ccc(C(F)(F)F)cc2)nc1N] | 63.97 ± 11.03 | 83.83 ± 11.52 | 77.10 ± 7.31 | 69.94 ± 8.54 | 71.39 ± 19.58 | 76.95 ± 6.87 |
| NK-64-3 | 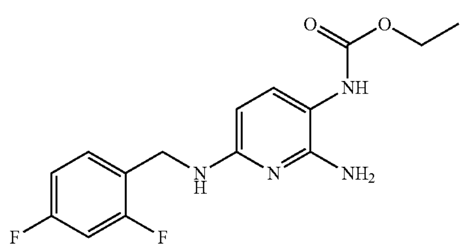 [SMILES: CCOC(=O)Nc1ccc(NCc2ccc(F)cc2F)nc1N] | 84.02 ± 21.86 | 92.98 ± 14.06 | 91.05 ± 19.84 | 78.04 ± 16.79 | 89.16 ± 4.40 | 90.71 ± 12.66 |
| NK-65-3 | 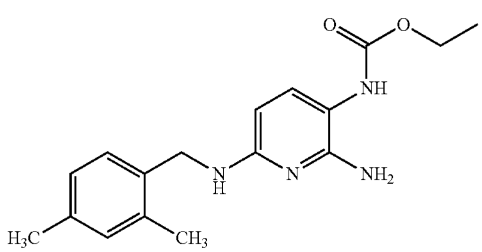 [SMILES: CCOC(=O)Nc1ccc(NCc2ccc(C)cc2C)nc1N] | 55.54 ± 11.33 | 56.87 ± 18.45 | 61.77 ± 9.82 | 87.89 ± 11.40 | 85.69 ± 13.19 | 65.74 ± 19.04 |

TABLE 1-continued

Protective effect of flupirtine derivatives to ameliorate etoposide-induced apoptosis in PC12 cells.

| Code | Structure | % Viability- 0.1 μM | % Viability- 0.3 μM | % Viability 1 μM | % Viability 3 μM | % Viability 10 μM | % Viability 30 μM |
| --- | --- | --- | --- | --- | --- | --- | --- |
| NK-66-3 | 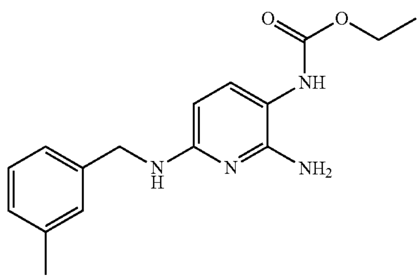 [SMILES: CCOC(=O)Nc1ccc(NCc2cccc(C)c2)nc1N] | 94.70 ± 25.84 | 109.64 ± 11.35 | 100.92 ± 17.45 | 82.28 ± 31.39 | 86.10 ± 26.91 | 106.85 ± 9.40 |
| NK-67-3 | 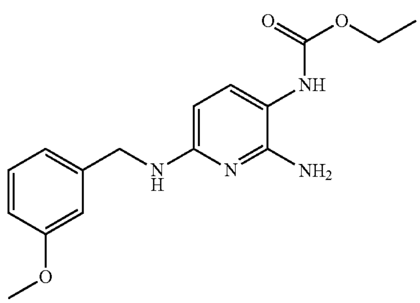 [SMILES: CCOC(=O)Nc1ccc(NCc2cccc(OC)c2)nc1N] | 59.19 ± 3.98 | 48.56 ± 9.49 | 82.78 ± 19.80 | 87.49 ± 15.02 | 70.09 ± 3.36 | 63.77 ± 14.04 |
| JG-4-5 | 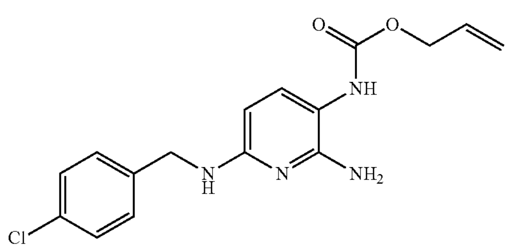 [SMILES: C=CCOC(=O)Nc1ccc(NCc2ccc(Cl)cc2)nc1N] | | | 87.16 ± 19.80 | 79.65 ± 7.48 | 84.28 ± 13.20 | 80.36 ± 24.14 |
| JG-32-3 | 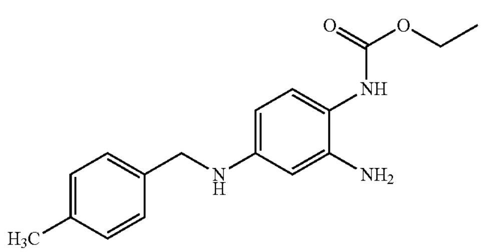 [SMILES: CCOC(=O)Nc1ccc(NCc2ccc(C)cc2)cc1N] | | | 109.93 ± 39.43 | 135.53 ± 30.06 | 122.96 ± 23.17 | 98.00 ± 22.93 |
| JG-33-4 | 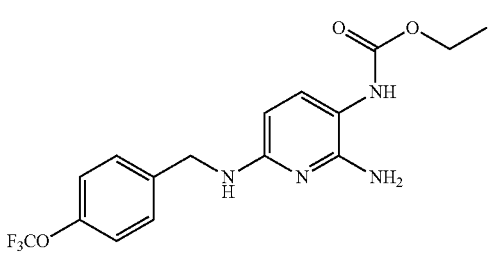 [SMILES: CCOC(=O)Nc1ccc(NCc2ccc(OC(F)(F)F)cc2)nc1N] | 71.34 ± 16.08 | 81.58 ± 10.87 | 79.79 ± 12.75 | 95.29 ± 14.59 | 88.87 ± 12.61 | 82.38 ± 12.63 |

TABLE 1-continued
Protective effect of flupirtine derivatives to ameliorate etoposide-induced apoptosis in PC12 cells.
| Code | Structure | % Viability- 0.1 μM | % Viability- 0.3 μM | % Viability 1 μM | % Viability 3 μM | % Viability 10 μM | % Viability 30 μM |
|---|---|---|---|---|---|---|---|
| JG-34-4 | 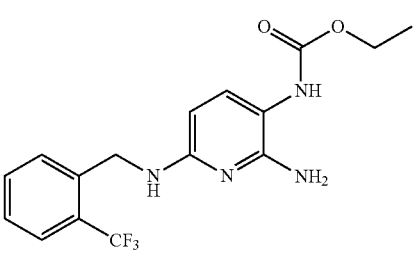 [SMILES: CCOC(=O)Nc1ccc(NCc2ccccc2C(F)(F)F)nc1N] | 74.63 ± 2.18 | 72.42 ± 16.45 | 95.10 ± 10.26 | 91.53 ± 12.90 | 95.43 ± 19.32 | 77.68 ± 6.86 |
| JG-35-4 | 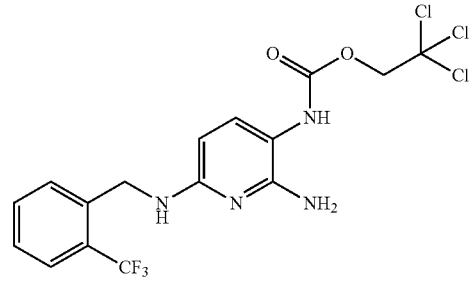 [SMILES: Nc1nc(NCc2ccccc2C(F)(F)F)ccc1NC(=O)OCC(Cl)(Cl)Cl] | | 92.24 ± 37.24 | 107.50 ± 7.32 | 93.25 ± 21.57 | 71.63 ± 20.76 | |
| JG-36-4 | 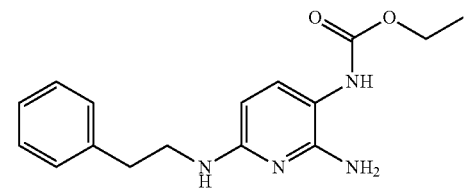 [SMILES: CCOC(=O)Nc1ccc(NCCc2ccccc2)nc1N] | 52.06 ± 11.50 | 56.85 ± 11.98 | 69.16 ± 7.10 | 49.96 ± 9.09 | 59.61 ± 9.05 | 60.52 ± 5.82 |
| JG-38-4 | 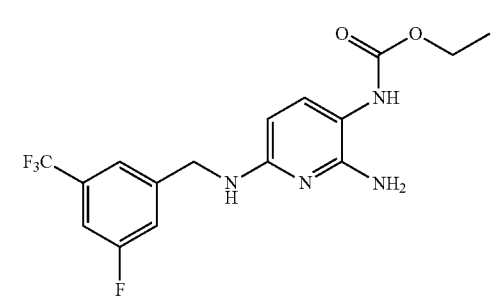 [SMILES: CCOC(=O)Nc1ccc(NCc2cc(F)cc(C(F)(F)F)c2)nc1N] | 69.02 ± 13.58 | 64.65 ± 12.49 | 69.72 ± 14.86 | 72.94 ± 13.25 | 90.06 ± 15.06 | 78.19 ± 12.54 |
| JG-41-4 | 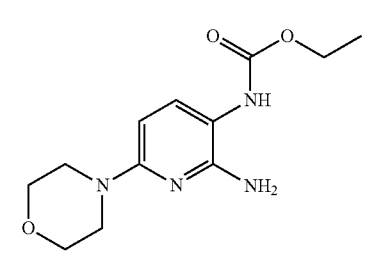 [SMILES: CCOC(=O)Nc1ccc(N2CCOCC2)nc1N] | | | 85.82 ± 15.50 | 88.74 ± 13.54 | 78.91 ± 14.26 | 63.86 ± 12.45 |

TABLE 1-continued

Protective effect of flupirtine derivatives to ameliorate etoposide-induced apoptosis in PC12 cells.

| Code | Structure | % Viability- 0.1 μM | % Viability- 0.3 μM | % Viability 1 μM | % Viability 3 μM | % Viability 10 μM | % Viability 30 μM |
|---|---|---|---|---|---|---|---|
| JG-48-6 | 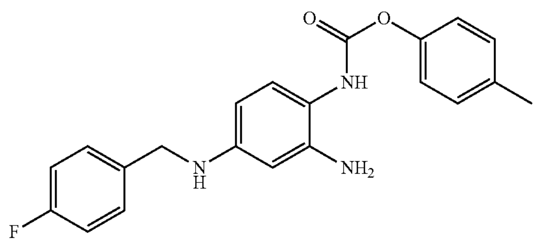 [SMILES: Cc1ccc(OC(=O)Nc2ccc(NCc3ccc(F)cc3)cc2N)cc1] | | | 69.97 ± 16.05 | 91.62 ± 10.99 | 83.71 ± 2.26 | 67.52 ± 10.20 |
| AM-2-3 | 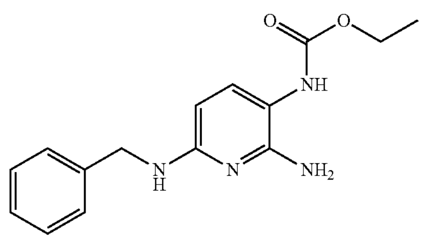 [SMILES: CCOC(=O)Nc1ccc(NCc2ccccc2)nc1N] | 83.24 ± 21.92 | 87.46 ± 1.65 | 93.46 ± 5.31 | 78.63 ± 10.85 | 92.16 ± 3.97 | 88.77 ± 5.02 |
| AM-4-3 | 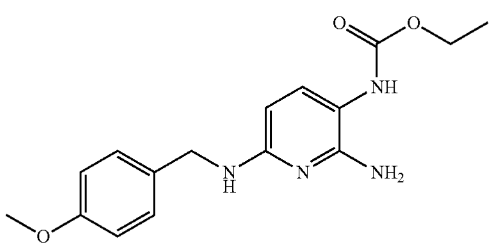 [SMILES: CCOC(=O)Nc1ccc(NCc2ccc(OC)cc2)nc1N] | 86.81 ± 3.14 | 81.40 ± 12.96 | 71.75 ± 25.67 | 79.68 ± 10.61 | 90.05 ± 16.26 | 105.98 ± 13.30 |
| AM-5-3 | 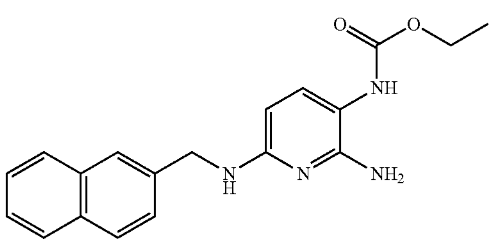 [SMILES: CCOC(=O)Nc1ccc(NCc2ccc3ccccc3c2)nc1N] | 70.47 ± 24.25 | 76.87 ± 20.84 | 81.65 ± 12.60 | 57.59 ± 6.35 | 65.13 ± 22.58 | 103.45 ± 1.31 |
| AM-8-3 | 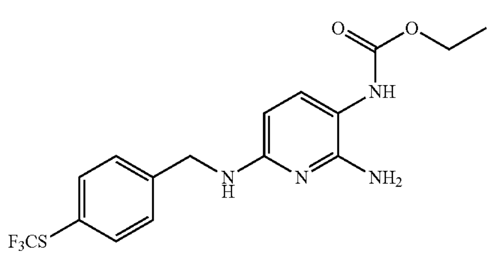 | 68.95 ± 9.99 | 92.64 ± 9.23 | 82.30 ± 7.02 | 79.24 ± 23.61 | 89.13 ± 2.16 | 110.22 ± 15.26 |

TABLE 1-continued

Protective effect of flupirtine derivatives to ameliorate etoposide-induced apoptosis in PC12 cells.

| Code | Structure | % Viability- 0.1 μM | % Viability- 0.3 μM | % Viability 1 μM | % Viability 3 μM | % Viability 10 μM | % Viability 30 μM |
| --- | --- | --- | --- | --- | --- | --- | --- |
| AM-11-3 | 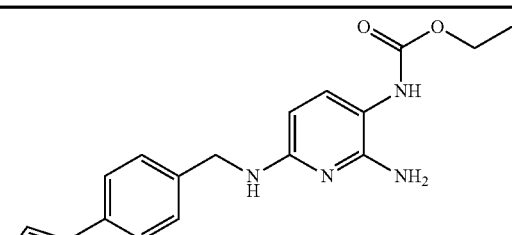 | 64.13 ± 16.62 | 77.10 ± 25.20 | 89.81 ± 30.11 | 76.08 ± 12.77 | 88.98 ± 29.11 | 35.28 ± 5.69 |
| AM-15-3 | 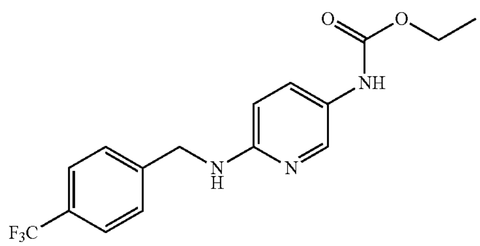 [SMILES: CCOC(=O)Nc1ccc(NCc2ccc(C(F)(F)F)cc2)nc1] | 59.67 ± 6.74 | 54.11 ± 12.70 | 58.98 ± 12.89 | 63.99 ± 7.87 | 66.36 ± 4.11 | 52.87 ± 8.69 |

TABLE 2

Protective effect of flupirtine derivatives to ameliorate serum starvation-induced apoptosis in PC12 cells

| Code | Structure | % Viability 1 μM | % Viability 3 μM | % Viability 10 μM | % Viability 30 μM |
| --- | --- | --- | --- | --- | --- |
| Vehicle | | 55.04 ± 8.99 | | | |
| NK-1-4 (Flu) | 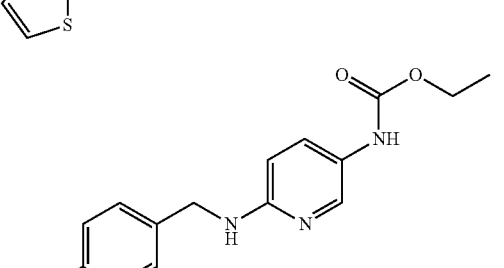 | 85.44 ± 14.02 | 82.05 ± 14.48 | 81.54 ± 12.97 | 89.89 ± 17.11 |
| NK-3-1 | 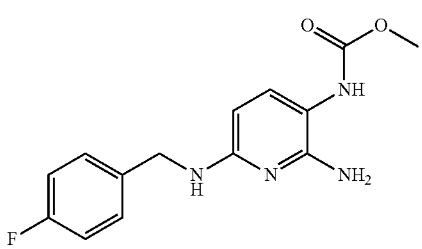 [SMILES: COC(=O)Nc1ccc(NCc2ccc(F)cc2)nc1N] | 76.91 ± 10.17 | 79.07 ± 8.28 | 72.18 ± 9.15 | 72.26 ± 16.36 |

TABLE 2-continued

Protective effect of flupirtine derivatives to ameliorate serum starvation-induced apoptosis in PC12 cells

| Code | Structure | % Viability 1 μM | % Viability 3 μM | % Viability 10 μM | % Viability 30 μM |
| --- | --- | --- | --- | --- | --- |
| NK-4-3 | 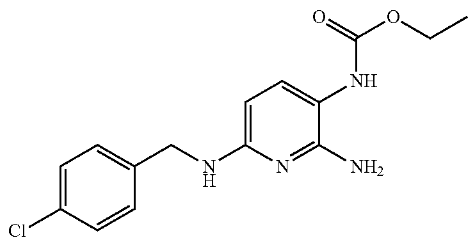 [SMILES: CCOC(=O)Nc1ccc(NCc2ccc(Cl)cc2)nc1N] | 77.99 ± 9.61 | 79.26 ± 5.50 | 86.55 ± 11.46 | 86.59 ± 5.32 |
| NK-8-1 | 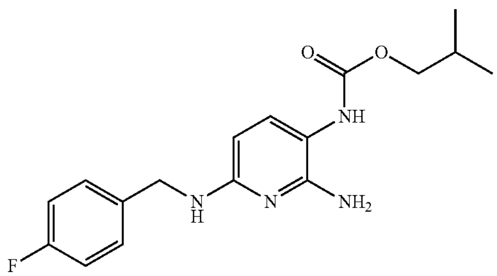 [SMILES: CC(C)COC(=O)Nc1ccc(NCc2ccc(F)cc2)nc1N] | 67.92 ± 12.64 | 77.42 ± 11.69 | 89.72 ± 6.68 | 88.27 ± 10.77 |
| NK-10-1 | 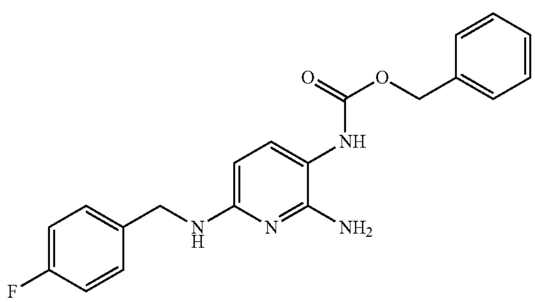 [SMILES: Nc1nc(NCc2ccc(F)cc2)ccc1NC(=O)OCc1ccccc1] | 93.43 ± 12.37 | 90.39 ± 11.18 | 92.65 ± 12.81 | 96.10 ± 15.26 |
| NK-12-1 | 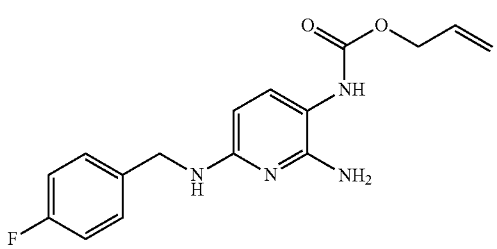 [SMILES: C=CCOC(=O)Nc1ccc(NCc2ccc(F)cc2)nc1N] | 107.70 ± 10.29 | 88.60 ± 8.26 | 82.15 ± 11.81 | 92.62 ± 12.29 |
| NK-16-3 | 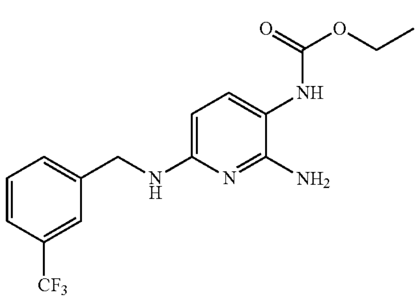 [SMILES: CCOC(=O)Nc1ccc(NCc2cccc(C(F)(F)F)c2)nc1N] | 83.59 ± 14.33 | 80.68 ± 8.11 | 86.89 ± 9.07 | 84.25 ± 16.07 |

TABLE 2-continued

Protective effect of flupirtine derivatives to ameliorate serum starvation-induced apoptosis in PC12 cells

| Code | Structure | % Viability 1 μM | % Viability 3 μM | % Viability 10 μM | % Viability 30 μM |
|---|---|---|---|---|---|
| NK-16-4 | 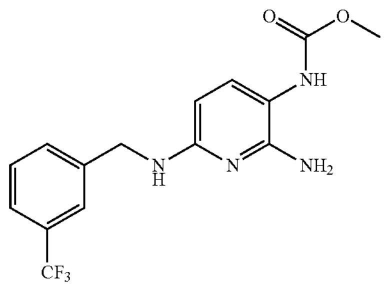 [SMILES: COC(=O)Nc1ccc(NCc2cccc(C(F)(F)F)c2)nc1N] | 92.06 ± 10.23 | 88.04 ± 8.56 | 97.84 ± 9.35 | 97.64 ± 1801 |
| NK-16-6 | 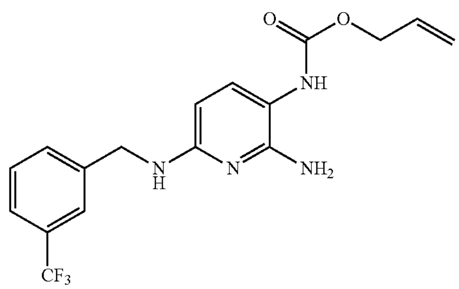 [SMILES: C=CCOC(=O)Nc1ccc(NCc2cccc(C(F)(F)F)c2)nc1N] | 77.08 ± 12.08 | 87.81 ± 10.04 | 92.00 ± 12.99 | 74.50 ± 11.92 |
| NK-17-3 | 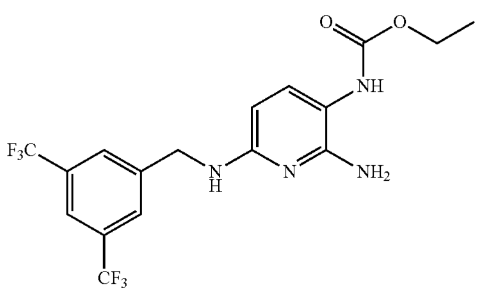 [SMILES: CCOC(=O)Nc1ccc(NCc2cc(C(F)(F)F)cc(C(F)(F)F)c2)nc1N] | 81.80 ± 8.69 | 72.83 ± 12.39 | 78.50 ± 6.27 | 57.86 ± 9.54 |
| NK-21-1 | 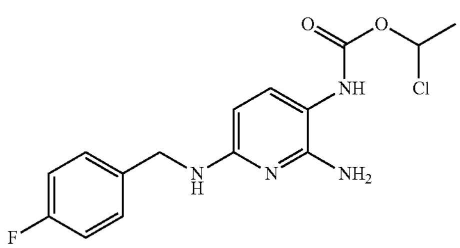 [SMILES: CC(Cl)OC(=O)Nc1ccc(NCc2ccc(F)cc2)nc1N] | 74.23 ± 11.53 | 75.59 ± 13.43 | 91.69 ± 6.31 | 84.02 ± 13.81 |
| NK-22-6 | 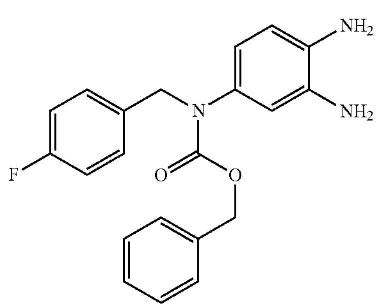 [SMILES: Nc1ccc(N(Cc2ccc(F)cc2)C(=O)OCc2ccccc2)cc1N] | 68.08 ± 8.86 | 82.53 ± 10.53 | 74.46 ± 8.48 | 37.36 ± 4.98 |

TABLE 2-continued
Protective effect of flupirtine derivatives to ameliorate serum starvation-induced apoptosis in PC12 cells
| Code | Structure | % Viability 1 μM | % Viability 3 μM | % Viability 10 μM | % Viability 30 μM |
|---|---|---|---|---|---|
| NK-22-13 (Ret) | 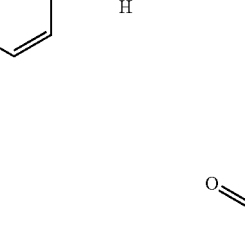 | 75.88 ± 14.98 | 77.92 ± 22.59 | 85.77 ± 17.88 | 76.19 ± 25.03 |
| NK-23-1 | 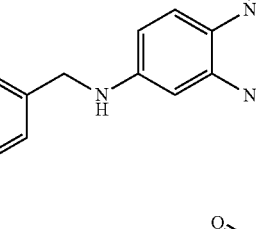 | 84.07 ± 11.85 | 83.62 ± 5.88 | 100.15 ± 15.84 | 106.47 ± 15.46 |
| NK-30-2 | 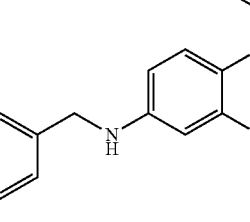 | 70.42 ± 3.39 | 78.31 ± 7.18 | 84.63 ± 4.75 | 76.25 ± 1.61 |
| JG-4-5 | 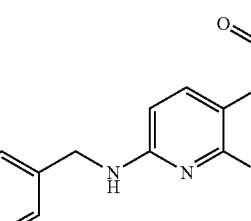 | 72.30 ± 1.45 | 95.19 ± 2.41 | 70.16 ± 9.45 | 71.12 ± 8.61 |
| JG-32-3 | 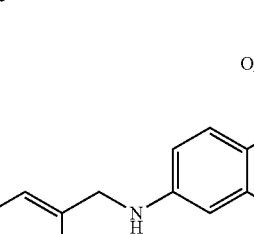 | 62.59 ± 16.72 | 79.54 ± 0.60 | 77.90 ± 1.34 | 71.33 ± 0.03 |

Characterization

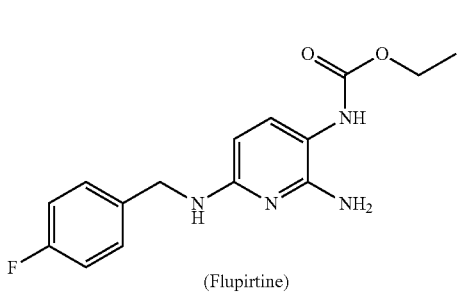

(Flupirtine)

Ethyl (2-amino-6-((4-fluorobenzyl)amino)pyridin-3-yl)carbamate

Bluish green solid

Yield—82%

$^1$H NMR (400 MHz, DMSO-d$_6$) –δ$_H$: 1.21 (3H, t, J=4.8 Hz, CH$_2$CH$_3$), 4.06 (2H, q, J=7.0 Hz, CH$_2$CH$_3$), 4.53 (2H, br. s, CH$_2$Ph), 5.92 (1H, d, J=8.6 Hz, ArH), 7.20 (2H, t, J=8.8 Hz, ArH), 7.34 (1H, br. s, —NH), 7.43-7.50 (3H, m, ArH), 8.15 (1H, br. s, NH), 8.52 (1H, br. s, NH), 13.06 (1H, br. s, NH).

$^{13}$C NMR (100 MHz, CDCl$_3$) –δ$_C$: 14.93, 44.94, 60.97, 115.67, 115.88, 128.58, 129.91, 130.00, 149.76, 155.60, 160.73.

$^{19}$F NMR——115.20

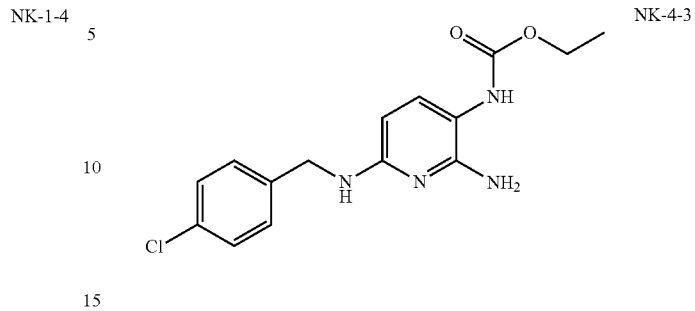

Ethyl (2-amino-6-((4-chlorobenzyl)amino)pyridin-3-yl)carbamate

Bluish green solid

Yield—65%

$^1$H NMR (400 MHz, DMSO-d$_6$) –δ$_H$: 1.21 (3H, br. s, CH$_2$CH$_3$), 4.05 (2H, q, J=6.50 Hz, CH$_2$CH$_3$), 4.55 (2H, br. s, CH$_2$Ph), 5.90 (1H, d, J=8.73 Hz, ArH), 7.36-7.47 (6H, m), 8.22 (1H, br. s, NH), 8.52 (1H, br. s, NH), 13.25 (1H, br. s, NH).

$^{13}$C NMR (100 MHz, DMSO-d$_6$) –δ$_C$: 14.93, 44.93, 60.97, 66.81, 94.04, 107.38, 128.94, 129.72, 132.39, 137.17, 149.65, 155.47.

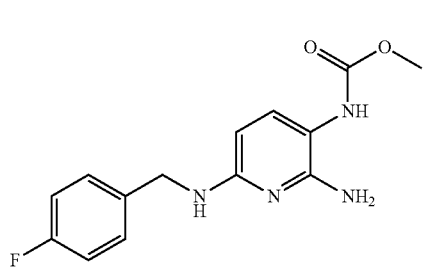

Methyl 6-(4-fluorobenzylamino)-2-aminopyridin-3-ylcarbamate

Bluish green solid

Yield—85%

$^1$H NMR (400 MHz, DMSO-d$_6$) –δ$_H$: 3.61 (3H, s, CH$_3$), 4.52 (2H, d, J=5.16 Hz, CH$_2$Ph), 5.91 (1H, d, J=8.77 Hz, ArH), 7.21 (2H, t, J=8.93 Hz, ArH), 7.34 (1H, br.s), 7.37-7.47 (3H, m, ArH), 8.17 (1H, br. s), 8.57 (1H, br. s, NH), 13.03 (1H, br. s, NH).

$^{13}$C NMR (100 MHz, DMSO-d$_6$) –δ$_C$: 44.95, 52.40, 94.10, 107.10, 115.66, 115.88, 130.06, 134.21, 143.42, 149.68, 155.96, 160.74, 163.15.

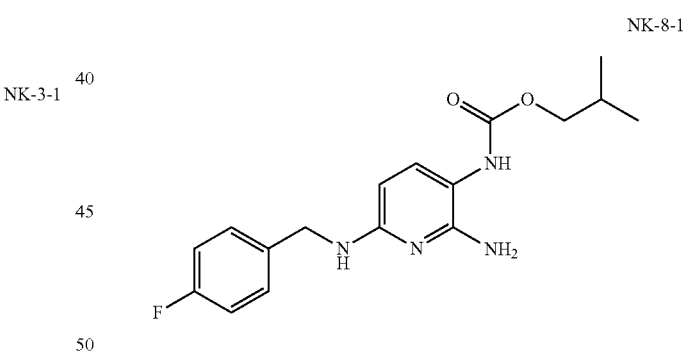

Isobutyl 6-(4-fluorobenzylamino)-2-aminopyridin-3-ylcarbamate

Bluish green solid

Yield—34%

$^1$H NMR (400 MHz, DMSO-d$_6$) –δ$_H$: 0.92 (6H, m), 1.88 (1H, br. s), 3.79 (2H, br. s), 4.53 (2H, br. s), 5.92 (1H, d, J=8.88 Hz), 7.20 (2H, t, J=8.98 Hz), 7.36 (1H, br.s), 7.43-7.49 (3H, m), 8.19 (1H, br. s), 8.54 (1H, br. s), 13.12 (1H, br. s)

$^{13}$C NMR (100 MHz, DMSO-d$_6$) –δ$_C$: 19.42, 27.98, 44.94, 66.81, 70.95, 94.09, 107.29, 115.66, 115.87, 129.95, 130.03, 134.20, 160.73, 163.14

$^{19}$F NMR——−115.23

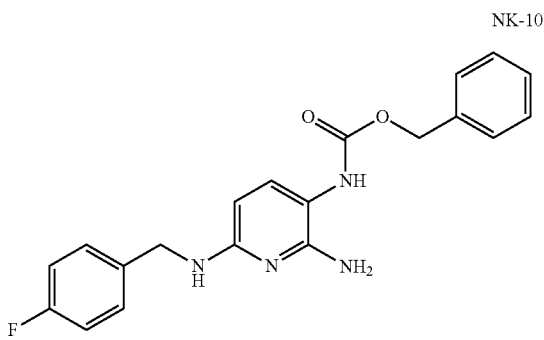

NK-10-1

Benzyl 6-(4-fluorobenzylamino)-2-aminopyridin-3-ylcarbamate

Bluish green solid

Yield—58%

$^1$H NMR (400 MHz, DMSO-d$_6$) –δ$_H$: 4.54 (2H, br. S, CH$_2$Ph), 5.09 (2H, br. s, CH$_2$Ph), 5.93 (1H, d. J=8.74 Hz, ArH), 7.20 (2H, t, J=8.61 Hz, ArH), 7.34-7.51 (9H, m), 8.22 (1H, br. s, NH), 8.70 (1H, br. s, NH)), 13.18 (1H, br. s, NH).

$^{13}$C NMR (100 MHz, DMSO-d$_6$) –δ$_C$: 44.96, 66.82, 94.20, 107.08, 115.87, 128.44, 128.84, 130.06, 134.20, 143.23, 149.63, 155.42, 160.74, 163.16.

$^{19}$F NMR——−115.22

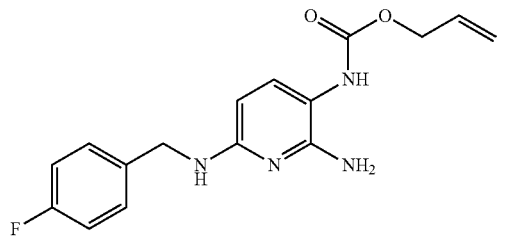

NK-12-1

Allyl 6-(4-fluorobenzylamino)-2-aminopyridin-3-ylcarbamate

Bluish green solid

Yield—78%

$^1$H NMR (400 MHz, DMSO-d$_6$) –δ$_H$: 4.53 (4H, m), 5.15-5.39 (2H, m), 5.91-5.98 (2H, m), 7.20 (2H, t, J=Hz, ArH), 7.38-7.48 (4H, m), 8.21 (1H, br. s, NH), 8.65 (1H, br. s, NH), 13.15 (1H, br. s, NH).

$^{13}$C NMR (100 MHz, DMSO-d$_6$) –δ$_C$: 44.94, 65.57, 91.40, 94.09, 107.08, 115.67, 115.88, 117.97, 129.95, 130.03, 133.71, 155.25, 160.73.

$^{19}$F NMR——−115.22

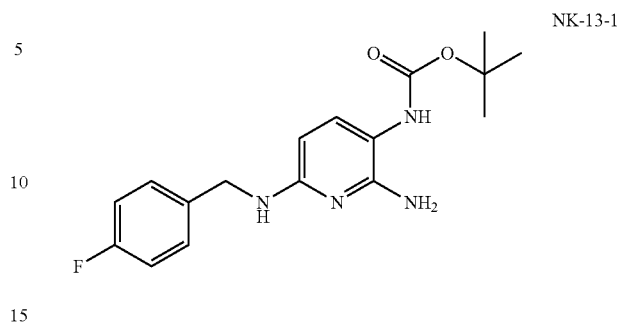

NK-13-1 tert-butyl 6-(4-fluorobenzylamino)-2-aminopyridin-3-ylcarbamate

Yellowish brown solid

Yield—25%

Rf=0.24 (1:1-H:EtOAc)

$^1$H NMR (400 MHz, DMSO-d$_6$) –δ$_H$: 1.42 (9H, s, CH$_3$), 4.35 (2H, d, J=6.11 Hz, CH$_2$Ph), 5.13 (2H, br. s), 5.68 (1H, d. J=8.53 Hz), 6.50 (1H, t, J=6.53 Hz), 7.01 (1H, d, J=7.35 Hz, ArH), 7.11 (2H, t, J=8.97 Hz, ArH), 7.35 (2H, t, J=6.67 Hz, ArH), 7.96 (1H, br. s).

$^{13}$C NMR (100 MHz, DMSO-d$_6$) –δ$_C$: 28.65, 44.10, 66.81, 78.71, 95.71, 107.48, 115.10, 115.30, 129.47, 137.75, 153.25, 154.73, 155.82, 160.20, 162.60.

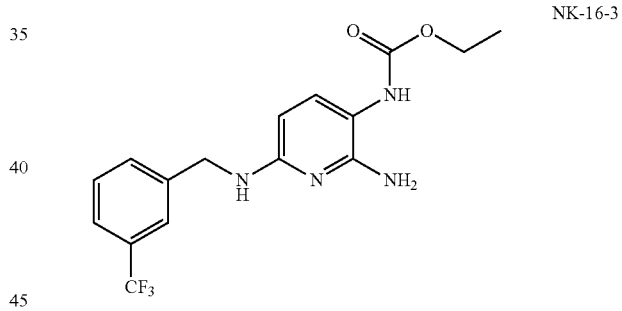

NK-16-3

Ethyl 6-(3-(trifluoromethyl)benzylamino)-2-aminopyridin-3-ylcarbamate

Green solid

Yield—32%

Rf=0.56 (Mobile Phase—10:1=dichloromethane:methanol)

$^1$H NMR (400 MHz, DMSO-d$_6$) –δ$_H$: 1.20 (3H, br. s, CH$_2$CH$_3$), 4.03 (2H, q, J=6.79 Hz, CH$_2$CH$_3$), 4.48 (2H, d, J=5.45 Hz, CH$_2$Ph), 5.36 (1H, br. s, NH$_2$), 5.73 (1H, d, J=8.34 Hz, ArH), 6.75 (1H, br. s, NH), 7.06 (1H, br. s, NH), 7.52-7.58 (2H, m, ArH), 7.63-7.68 (2H, m, ArH), 8.22 (1H, s, ArH).

$^{13}$C NMR (100 MHz, DMSO-d$_6$) –δ$_C$: 15.04, 44.38, 60.44, 95.51, 107.31, 123.46, 123.61, 124.02, 126.17, 129.59, 131.81, 136.56, 143.08, 153.26, 155.56.

M/Z (ESI)—355.1 (100%) [MH$^+$], 356.2 (20%), 377.1 [MNa$^+$] (15%)

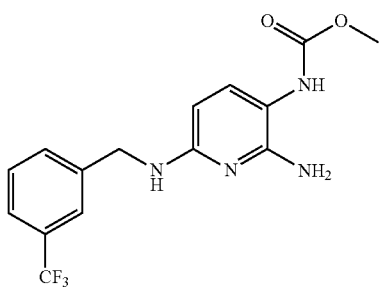

NK-16-4

Methyl 6-(3-(trifluoromethyl)benzylamino)-2-aminopyridin-3-ylcarbamate

Green solid

Yield—30%

Rf=0.53 (Mobile Phase—10:1=dichloromethane:methanol)

$^1$H NMR (400 MHz, DMSO-d$_6$) –δ$_H$: 3.58 (3H, s, CH$_3$), 4.48 (2H, d, J=5.97 Hz, CH$_2$Ph), 5.31 (1H, br. s, NH$_2$), 5.71 (1H, d, J=8.30 Hz, ArH), 6.73 (1H, br. s, NH), 7.04 (1H, br. s, NH), 7.52-7.67 (4H, m, ArH), 8.22 (1H, s, ArH).

$^{13}$C NMR (100 MHz, DMSO-d$_6$) –δ$_C$: 31.15, 44.35, 52.00, 95.46, 107.15, 123.66, 124.06, 126.17, 128.88, 129.18, 129.50, 129.61, 131.82, 143.09, 156.03.

$^{19}$F NMR—–60.94

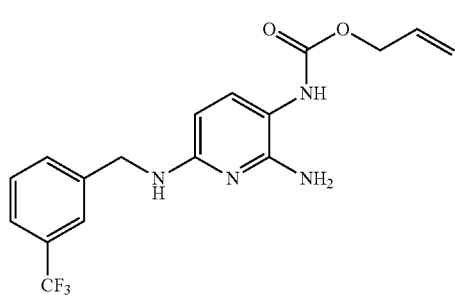

NK-16-6

Allyl 6-(3-(trifluoromethyl)benzylamino)-2-aminopyridin-3-ylcarbamate

Green solid

Yield—31%

Rf=0.69 (Mobile Phase—10:1=dichloromethane:methanol)

$^1$H NMR (400 MHz, CDCl$_3$) –δ$_H$: 4.49 (3H, m, CH$_2$CHCH$_2$), 4.64 (2H, d, J=4.46 Hz, CH$_2$Ph), 4.95 (1H, br. s, NH), 5.30 (2H, m, CH$_2$CHCH$_2$), 5.76 (1H, d, J=8.23 Hz, ArH), 5.97 (1H, br. s, NH), 6.24 (1H, br. s, NH), 7.16 (1H, d, J=7.39 Hz, ArH), 7.44 (1H, m, ArH), 7.53 (2H, d, J=7.54 Hz, ArH), 7.60 (1H, s, ArH).

$^{13}$C NMR (100 MHz, CDCl$_3$) –δ$_C$: 45.91, 66.17, 96.28, 107.55, 118.26, 122.77, 123.96, 125.47, 129.01, 130.56, 132.43, 137.45, 140.55, 153.62, 155.20, 156.24.

$^{19}$F NMR—–60.95

M/Z (ESI)—367.1 (100%) [MH$^+$], 368.2 (20%), 389.1 (50%) [MNa$^+$]

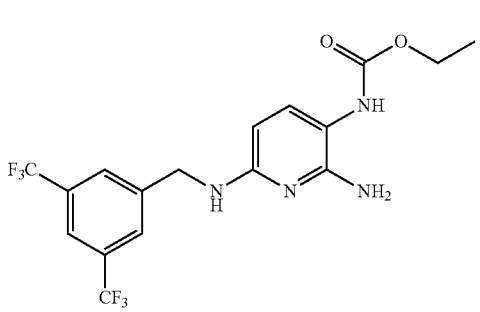

NK-17-3

Ethyl (2-amino-6-((3,5-bis(trifluoromethyl)benzyl)amino)pyridin-3-yl)carbamate

Green solid

Yield—22%

Rf=0.30 (Mobile Phase—1:1=hexane:ethyl acetate)

$^1$H NMR (400 MHz, DMSO-d$_6$) –δ$_H$: 1.20 (3H, t, J=6.72 Hz, CH$_2$CH$_3$), 4.03 (2H, q, J=7.14 Hz, CH$_2$CH$_3$), 4.55 (2H, d, J=6.30 Hz, CH$_2$Ph), 5.25 (2H, br. s, NH$_2$), 5.73 (1H, d, J=8.27 Hz, ArH), 6.78 (1H, t, J=6.52 Hz, NH), 7.05 (1H, d, J=7.97 Hz, ArH), 7.94 (1H, s, ArH), 8.02 (2H, s, ArH), 8.21 (1H, br. s, NH).

$^{13}$C NMR (100 MHz, DMSO-d$_6$) –δ$_C$: 15.06, 44.03, 60.41, 95.65, 107.44, 120.68, 122.57, 125.28, 128.47, 130.23, 130.56, 145.66, 155.53.

$^{19}$F NMR—–61.23 m/z (ESI)—423.1 (75%) [MH$^+$], 445.1 (100%) [MNa$^+$], 446.2 (20%)

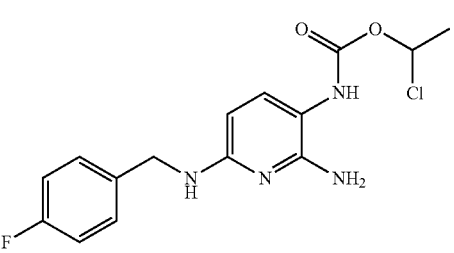

NK-21-1

1-chloroethyl 6-(4-fluorobenzylamino)-2-aminopyridin-3-ylcarbamate

Bluish green solid

Yield—58%

$^1$H NMR (400 MHz, DMSO-d$_6$) –δ$_H$:

$^{13}$C NMR (100 MHz, DMSO-d$_6$) –δ$_C$:

m/z (ESI)—233.1 (100%) [Fragmentation of carbamate group], 234.2 (15%), 339.1 (100%) [MH$^+$], 341.0 (10%)

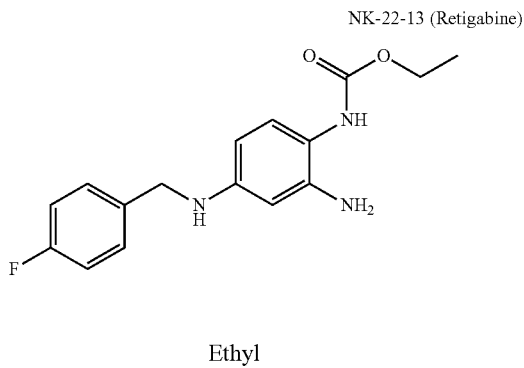

NK-22-13 (Retigabine)

Ethyl (2-amino-4-((4-fluorobenzyl)amino)phenyl)carbamate

Purple solid
Yield—Quant
$^1$H NMR (400 MHz, CDCl$_3$) –δ$_H$: 1.31 (3H, t, J=7.24 Hz, CH$_2$CH$_3$), 3.61 (2H, br. s, NH$_2$), 4.21 (2H, q, J=7.12 Hz, CH$_2$CH$_3$), 4.27 (2H, br. s, CH$_2$Ph), 6.02-6.09 (3H, m), 6.94 (1H, d, J=8.40 Hz, ArH), 7.04 (2H, t, J=8.68 Hz, ArH), 7.33 (2H, t, J=8.61 Hz, ArH).

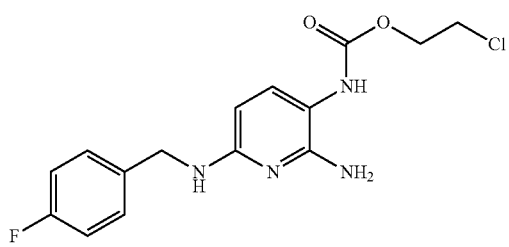

NK-23-1

2-chloroethyl 6-(4-fluorobenzylamino)-2-aminopyridin-3-ylcarbamate

Green solid
Yield—3%
Rf=0.72 (Mobile Phase—10:1=DCM:methanol)
$^1$H NMR (400 MHz, DMSO-d$_6$) –δ$_H$: 3.84 (2H, br. s), 4.28 (2H, br. s), 4.53 (2H, br. s), 5.93 (1H, d, J=8.72 Hz), 7.20 (2H, t, J=8.32 Hz), 7.34 (1H, br. s), 7.43-7.49 (3H, m), 8.16 (1H, br. s), 8.74 (1H, s), 13.05 (1H, br. s).
$^{13}$C NMR (100 MHz, CDCl$_3$) –δ$_C$: 42.17, 45.71, 65.05, 96.16, 107.02, 115.50, 128.91, 134.88, 137.52, 153.46, 154.89, 156.39, 160.78, 163.21.
M/Z (ESI)—339.1 (100%) [MH$^+$], 340.1 (25%), 341.1 (35%).

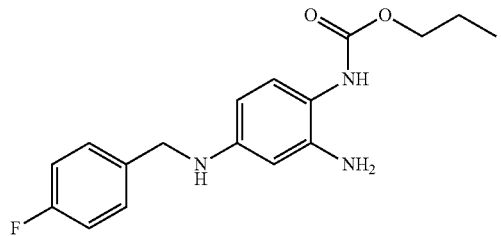 [SMILES: CCCOC(=O)Nc1ccc(NCc2ccc(F)cc2)cc1N]

NK-30-2

Propyl (2-amino-4-((4-fluorobenzyl)amino)phenyl)carbamate

Brown solid
Yield—36%
$^1$H NMR (400 MHz, DMSO-d$_6$) –δ$_H$: 0.90 (3H, br. s, CH$_2$CH$_3$), 1.58 (2H, br. s, CH$_2$), 3.93 (2H, t, J=5.69 Hz, CH$_2$), 4.17 (2H, d, J=4.68 Hz, CH$_2$Ph), 4.53 (2H, br. s, NH$_2$), 5.81 (1H, d, J=7.83 Hz, ArH), 5.92 (2H, m), 6.69 (1H, d, J=7.30 Hz, ArH), 7.12 (2H, t, J=8.53 Hz, ArH), 7.36 (2H, t, J=6.61 Hz, ArH), 8.17 (1H, br. s, NH).
$^{13}$C NMR (100 MHz, DMSO-d$_6$) –δ$_C$: 10.75, 22.49, 46.32, 65.83, 102.12, 113.47, 115.20, 115.41, 129.26, 129.34, 137.25, 137.30, 160.24, 164.72.

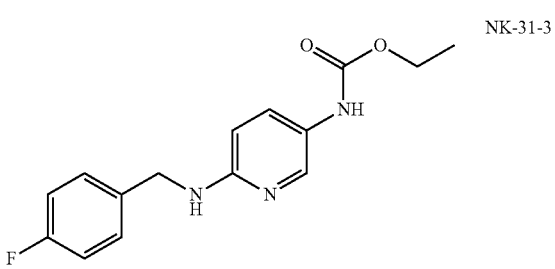

NK-31-3

Ethyl (4-((4-fluorobenzyl)amino)phenyl)carbamate

Brown solid
Yield—24%
$^1$H NMR (400 MHz, CDCl$_3$) δ$_H$: 1.32 (3H, t, J=6.79 Hz, CH$_2$CH$_3$), 4.23 (2H, q, J=7.51 Hz, CH$_2$CH$_3$), 4.49 (2H, d, J=4.31 Hz, CH$_2$Ph), 5.53 (1H, br. s, NH$_2$), 6.43-6.49 (2H, m), 7.04 (2H, t, J=8.36 Hz, ArH), 7.34 (2H, t, J=6.25 Hz, ArH), 7.71 (1H, br. s, NH), 8.05 (1H, s, ArH).
$^{13}$C NMR (100 MHz, DMSO-d$_6$) –δ$_C$: 15.00, 44.29, 60.61, 109.22, 115.26, 126.02, 129.67, 131.54, 136.75, 154.48, 160.35, 162.75.

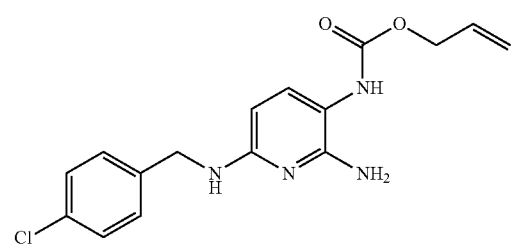 [SMILES: C=CCOC(=O)Nc1ccc(NCc2ccc(Cl)cc2)nc1N]

JG-4-5

Allyl (2-amino-4-((4-chlorobenzyl)amino)phenyl)carbamate

Greenish solid
Yield—61%
$^1$H NMR (400 MHz, DMSO-d$_6$) –δ$_H$: 4.47 (2H, d, J=4.40 Hz, CH$_2$), 4.54 (2H, d, J=3.79 Hz, CH$_2$), 5.22 (1H, d, J=10.21 Hz, CH$_2$), 5.35 (1H, d, J=16.97 Hz, CH$_2$), 5.80 (1H, d, J=8.50 Hz, ArH), 5.95 (1H, m, CH), 6.31 (2H, br. s, NH$_2$), 7.24 (1H, d, J=7.90 Hz, ArH), 7.38-7.42 (5H, m, ArH, NH), 8.50 (1J, br. s, NH).

$^{13}$C NMR (100 MHz, DMSO-d$_6$) –δ$_C$: 44.52, 65.27, 94.94, 107.09, 117.76, 128.69, 129.60, 131.81, 133.91, 139.04, 151.74, 153.09, 155.23.

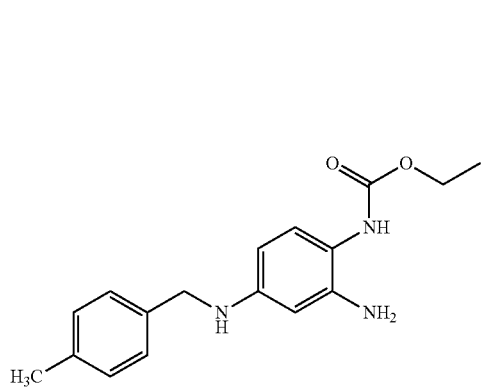 [SMILES: CCOC(=O)Nc1ccc(NCc2ccc(C)cc2)cc1N]

JG-32-3

Ethyl (2-amino-4-((4-methylbenzyl)amino)phenyl)carbamate

Bluish green solid

Yield—8%

$^1$H NMR (400 MHz, MeOD-d$_4$) –δ$_H$: 1.29 (3H, br. s, CH$_2$CH$_3$), 4.16 (2H, q, J=7.13 Hz, CH$_2$CH$_3$), 7.10- 7.16 (4H, m, ArH), 7.27 (1H, s, ArH).

$^{13}$C NMR (100 MHz, DMSO-d$_6$) –δ$_C$: 14.90, 21.07, 33.16, 61.00, 66.80, 107.08, 107.19, 128.67, 129.49, 135.79, 136.31, 148.59.

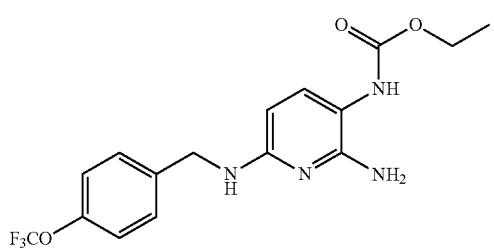

JG-33-4

Ethyl (2-amino-6-((4-(trifluoromethoxy)benzyl)amino)pyridin-3-yl)carbamate

Bluish green solid

Yield—68%

$^1$H NMR (400 MHz, DMSO-d$_6$) –δ$_H$: 1.22 (3H, t, J=7.94 Hz, CH$_2$CH$_3$), 4.06 (2H, q, J=7.28 Hz, CH$_2$CH$_3$), 4.58 (2H, d, J=4.00 Hz, CH$_2$Ph), 5.91 (1H, d, J=8.76 Hz, ArH), 7.30-7.53 (6H, m), 8.15 (1H, br. s, NH), 8.53 (1H, br. s, NH), 13.04 (1H, br. s, NH).

$^{13}$C NMR (100 MHz, DMSO-d$_6$) –δ$_C$: 14.93, 44.91, 60.98, 94.01, 107.39, 119.26, 121.63, 121.80, 129.77, 137.62, 143.26, 148.02, 149.63.

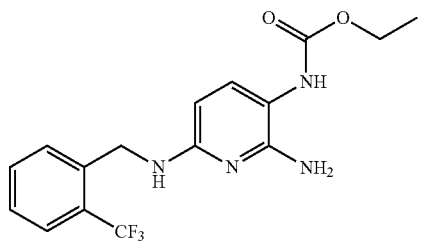

JG-34-4

Ethyl (2-amino-6-((2-(trifluoromethyl)benzyl)amino)pyridin-3-yl)carbamate

Bluish solid

Yield—38%

$^1$H NMR (400 MHz, DMSO-d$_6$) –δ$_H$: 1.22 (3H, t, J=7.94 Hz, CH$_2$CH$_3$), 4.06 (2H, q, J=7.08 Hz, CH$_2$CH$_3$), 4.63 (2H, br. s, CH$_2$Ph), 5.79 (1H, d, J=8.50 Hz, ArH), 7.44 (1H, br. s, NH), 7.54 (1H, t, J=7.78 Hz, ArH), 7.60 (1H, d, J=7.83 Hz, ArH), 7.70 (1H, t, J=7.72 Hz, ArH), 7.79 (1H, d, J=7.98 Hz, ArH), 8.52 (1H, br. s, NH).

$^{13}$C NMR (100 MHz, DMSO-d$_6$) –δ$_C$: 14.94, 43.10, 60.99, 93.39, 107.84, 123.45, 126.18, 126.67, 127.26, 128.61, 129.60, 133.45, 136.02, 149.73, 155.48.

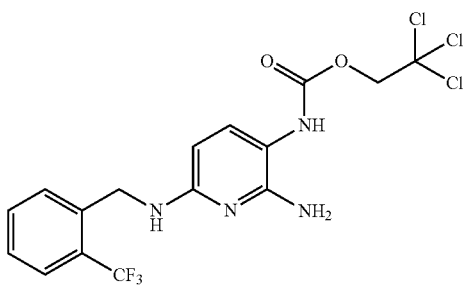

JG-35-4

2,2,2-trichloroethyl (2-amino-6-((2-(trifluoromethyl)benzyl)amino)pyridin-3-yl)carbamate Greyish solid Yield—58%

$^1$H NMR (400 MHz, DMSO-d$_6$) –δ$_H$: 4.67 (2H, s, CH$_2$), 4.86 (2H, br. s, CH$_2$Ph), 5.83 (1H, d, J=8.75 Hz, ArH), 7.48-7.61 (3H, m, ArH), 7.70 (1H, t, J=7.29 Hz, ArH), 7.79 (1H, d, J=8.14 Hz, ArH), 8.07 (1H, br. s, NH), 9.13 (1H, br. s, NH).

$^{13}$C NMR (100 MHz, DMSO-d$_6$) –δ$_C$: 43.09, 74.47, 93.67, 96.24, 106.86, 126.17, 126.68, 126.97, 127.27, 128.63, 129.63, 133.45, 143.42, 149.81, 153.96.

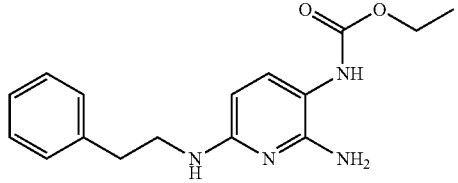

JG-36-4

Ethyl (2-amino-6-(phenethylamino)pyridin-3-yl)carbamate

Bluish solid
Yield—15%
$^1$H NMR (400 MHz, CDCl$_3$) –δ$_H$: 1.28 (3H, t, J=6.73 Hz, CH$_2$CH$_3$), 2.94 (2H, t, J=7.32 Hz, —CH$_2$), 3.42 (2H, t, J=7.33 Hz, CH$_2$Ph), 4.19 (2H, q, J=6.96 Hz, CH$_2$CH$_3$), 5.68 (1H, d, J=8.90 Hz, ArH), 6.70 (2H, br. s, NH$_2$), 7.23-7.26 (3H, m, ArH), 7.31-7.44 (4H, m, ArH, NH), 13.76 (1H, br. s, NH).
$^{13}$C NMR (100 MHz, CDCl$_3$) –δ$_C$: 14

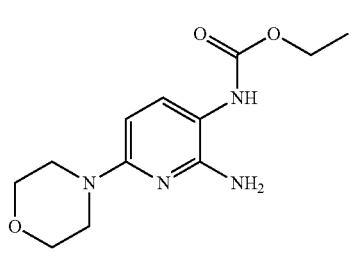

JG-38-4

Ethyl (2-amino-6-((3-fluoro-5-(trifluoromethyl)benzyl)amino)pyridin-3-yl)carbamate Bluish solid
Yield—65%
$^1$H NMR (400 MHz, DMSO-d$_6$) –δ$_H$: 1.21 (3H, br. s, CH$_2$CH$_3$), 4.06 (2H, q, J=6.80 Hz, CH$_2$CH$_3$), 4.68 (2H, br. s, CH$_2$Ph), 5.94 (1H, d, J=8.76 Hz, ArH), 7.41-7.51 (2H, m), 7.60-7.68 (3H, m), 8.31 (1H, br. s, NH), 8.56 (1H, br. s, NH), 13.35 (1H, br. s, NH).
$^{13}$C NMR (100 MHz, DMSO-d$_6$) –δ$_C$: 14.92, 44.71, 60.99, 66.81, 93.91, 107.85, 112.36, 118.98, 120.81, 122.39, 125.18, 131.29, 143.31, 161.24, 163.69.
$^{19}$F NMR—−61.15, −110.51

JG-41-4

Ethyl (2-amino-6-morpholinopyridin-3-yl)carbamate

Brownish solid
Yield—59%
$^1$H NMR (400 MHz, CDCl$_3$) –δ$_H$: 1.32 (3H, t, J=7.00 Hz, CH$_2$CH$_3$), 3.64 (4H, t, J=4.83 Hz, CH$_2$), 3.87 (4H, t, J=5.09 Hz, CH$_2$), 4.23 (2H, q, J=7.11 Hz, CH$_2$CH$_3$), 5.96 (1H, d, J=8.74 Hz, ArH), 7.38 (2H, br. s, NH$_2$), 7.72 (1H, br.s, ArH), 13.55 (1H, br. s, NH).
$^{13}$C NMR (100 MHz, CDCl$_3$) –δ$_C$: 14.54, 47.29, 62.10, 65.91, 67.09, 77.23, 94.86, 155.23.

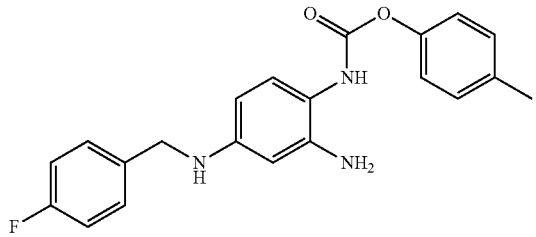

JG-48-6 p-tolyl (2-amino-4-((4-fluorobenzyl)amino)phenyl) carbamate

Brownish solid
Yield—18%
$^1$H NMR (400 MHz, DMSO-d$_6$) –δ$_H$: 2.18 (3H, s, CH$_3$), 4.19 (2H, d, J=6.00 Hz, CH$_2$Ph), 5.88 (1H, t, J=6.28 Hz, NH), 6.19-6.22 (2H, m, ArH), 6.61-6.66 (3H, m, ArH), 6.95 (2H, d, J=8.06 Hz, ArH), 7.14 (2H, t, J=8.91 Hz, ArH), 7.38 (2H, t, J=8.62 Hz, ArH), 10.12 (2H, m).
$^{13}$C NMR (100 MHz, DMSO-d$_6$) –δ$_C$: 20.56, 47.03, 94.31, 105.77, 109.30, 115.27, 115.49, 121.21, 127.44, 129.41, 130.13, 131.08, 137.18, 144.06, 155.58, 155.90, 106.27, 162.67.

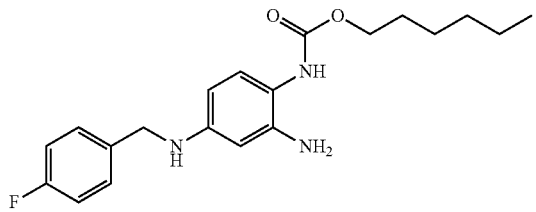

NK-34-2

Hexyl (2-amino-4-((4-fluorobenzyl)amino)phenyl)carbamate

Brownish solid
Yield—Quant
$^1$H NMR (400 MHz, CDCl$_3$) –δ$_H$: 0.90 (3H, t, J=6.58 Hz, CH$_3$), 1.33 (6H, m, CH$_2$), 1.66 (2H, m, CH$_2$), 3.72 (2H, br. s, NH$_2$), 4.13 (2H, t, J=6.77 Hz, CH$_2$), 4.24 (2H, br. s, CH$_2$Ph), 5.99 (1H, d, J=2.26 Hz, ArH), 6.05 (1H, dd, J=6.29 Hz, 2.15 Hz, ArH), 6.18 (1H, br. s, NH), 6.91 (1H, d, J=8.06 Hz, ArH), 7.03 (2H, d, J=8.67 Hz, ArH), 7.31 (2H, t, J=8.42 Hz, ArH).
$^{13}$C NMR (100 MHz, CDCl$_3$) –δ$_C$: 14.04, 22.58, 25.53, 28.95, 31.48, 47.60, 65.61, 104.32, 115.30, 115.51, 128.88, 128.96, 135.12, 135.15, 147.68, 160.78, 163.21.

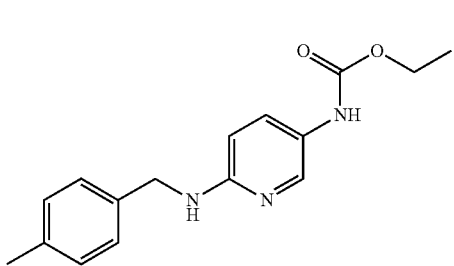

NK-39-3

Ethyl (6-((4-methylbenzyl)amino)pyridin-3-yl)carbamate

Purple solid

Yield—38%

$^1$H NMR (400 MHz, DMSO-d$_6$) –δ$_H$: 1.21 (3H, t, J=7.08 Hz, CH$_2$CH$_3$), 2.26 (3H, s, CH$_3$), 4.07 (2H, q, J=7.10 Hz, CH$_2$CH$_3$), 4.37 (2H, d, J=6.07 Hz, CH$_2$Ph), 6.45 (1H, d, J=8.87 Hz, ArH), 6.79 (1H, t, J=5.99 Hz, NH), 7.10 (2H, d, J=7.86 Hz, ArH), 7.20 (2H, d, J=7.97 Hz, ArH), 7.44 (1H, d, J=7.55 Hz, ArH), 7.97 (1H, s, ArH), 9.16 (1H, br. s, NH).

$^{13}$C NMR (100 MHz, DMSO-d$_6$) –δ$_C$: 15.03, 21.12, 44.68, 60.45, 108.04, 127.63, 129.15, 130.36, 135.84, 138.13, 139.48, 154.57, 155.67.

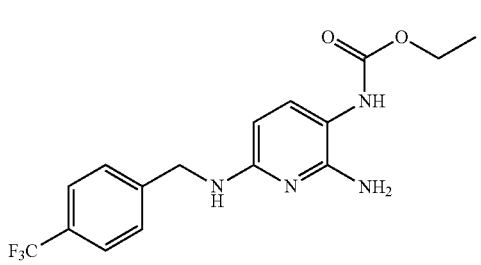

NK-40-3

Ethyl (2-amino-6-((4-(trifluoromethyl)benzyl)amino)pyridin-3-yl)carbamate

Bluish green solid

Yield—53%

$^1$H NMR (400 MHz, DMSO-d$_6$) –δ$_H$: 1.22 (3H, t, J=6.26 Hz, CH$_2$CH$_3$), 4.05 (2H, q, J=6.98 Hz, CH$_2$CH$_3$), 4.67 (2H, d, J=4.25 Hz, CH$_2$Ph), 5.91 (1H, d, J=8.80 Hz, ArH), 7.42-7.49 (2H, m), 7.61 (2H, t, J=8.09 Hz, ArH), 7.74 (2H, t, J=8.13 Hz, ArH), 8.37 (1H, br. s, NH), 8.56 (1H, br. s, NH), 13.43 (1H, br. s, NH).

$^{13}$C NMR (100 MHz, DMSO-d$_6$) –δ$_C$: 14.93, 45.14, 60.99, 93.97, 107.54, 123.36, 125.84, 125.07, 128.25, 128.46, 143.13, 149.62, 155.49.

$^{19}$F NMR—−60.87

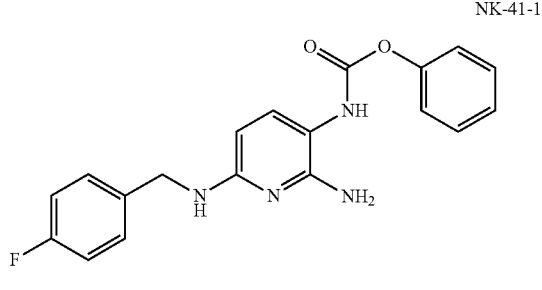 [SMILES: Nc1nc(NCc2ccc(F)cc2)ccc1NC(=O)Oc1ccccc1]

NK-41-1

Phenyl (2-amino-6-((4-fluorobenzyl)amino)pyridin-3-yl)carbamate

Greenish solid

Yield—37%

$^1$H NMR (400 MHz, DMSO-d$_6$) –δ$_H$: 4.38 (2H, d, J=6.20 Hz, CH$_2$Ph), 5.39 (2H, br. s, NH$_2$), 5.71 (1H, d, J=8.31 Hz, ArH), 6.61 (1H, t, J=6.30 Hz, NH), 7.08-7.24 (6H, m, ArH), 7.34-7.42 (4H, m, ArH), 8.78 (1H, br. s, NH).

$^{13}$C NMR (100 MHz, CDCl$_3$) –δ$_C$: 45.72, 96.39, 99.98, 107.10, 115.31, 115.52, 121.51, 125.63, 128.85, 128.93, 129.37, 134.82, 137.30, 150.80, 153.14, 156.31, 160.80, 163.24.

$^{19}$F NMR—−115.62

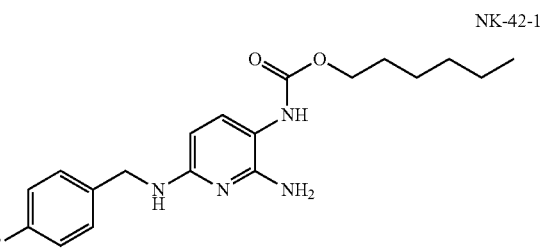

NK-42-1

Hexyl (2-amino-6-((4-fluorobenzyl)amino)pyridin-3-yl)carbamate

Bluish green solid

Yield—61%

$^1$H NMR (400 MHz, DMSO-d$_6$) –δ$_H$: 0.87 (3H, br. s, CH$_3$), 1.25-1.34 (6H, m, CH$_2$), 1.58 (2H, br. s, CH$_2$), 4.00 (2H, q, J=5.89 Hz, CH$_2$CH$_3$), 4.54 (2H, d, J=4.72 Hz, CH$_2$Ph), 5.92 (1H, d, J=8.80 Hz, ArH), 7.20 (2H, t, J=8.90 Hz, ArH), 7.38-7.47 (4H, m), 8.24 (1H, br. s, NH), 8.53 (1H, br. s, NH), 13.22 (1H, br. s, NH).

$^{13}$C NMR (100 MHz, DMSO-d$_6$) –δ$_C$: 14.36, 22.49, 25.50, 31.39, 44.93, 65.06, 94.11, 107.28, 115.66, 115.87, 129.94, 130.03, 134.23, 149.63, 155.59, 160.73, 163.15.

¹⁹F NMR—−115.23

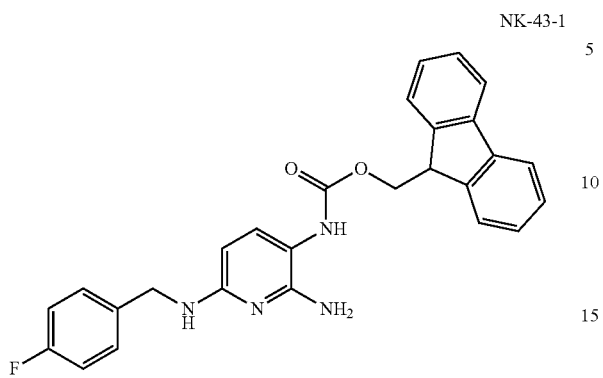

NK-43-1

(9H-fluoren-9-yl)methyl (2-amino-6-((4-fluorobenzyl)amino)pyridin-3-yl)carbamate Greenish solid Rf=0.43 (20:1—DCM:MeOH)

Yield—13%

¹H NMR (400 MHz, DMSO-d$_6$) −δ$_H$: 4.22-4.38 (5H, m, CH$_2$), 5.21 (2H, br. s, NH$_2$), 5.69 (1H, d, J=8.21 Hz, ArH), 6.57 (1H, t, J=6.20 Hz, NH), 7.00 (1H, d, J=7.93 Hz, ArH), 7.11 (2H, t, J=8.90 Hz, ArH), 7.34-7.45 (6H, m, ArH), 7.75-7.92 (4H, m, ArH), 8.41 (1H, br. s, NH).

¹³C NMR (100 MHz, DMSO-d$_6$) −δ$_C$: 44.10, 47.20, 66.09, 95.71, 115.13, 115.34, 120.50, 120.59, 121.85, 127.53, 127.75, 128.10, 137.70, 137.73, 137.88, 139.87, 141.20, 144.32, 160.22, 162.62.

NK-45-1

Prop-2-yn-1-yl (2-amino-6-((4-fluorobenzyl)amino)pyridin-3-yl)carbamate

Bluish green solid

Yield—68%

¹H NMR (400 MHz, DMSO-d$_6$) −δ$_H$: 4.53 (2H, d, J=4.00 Hz, CH$_2$Ph), 4.69 (2H, s, CH$_2$), 5.92 (1H, d, J=8.85 Hz, ArH), 7.20 (2H, t, J=8.90 Hz, ArH), 7.37-7.49 (4H, m), 8.21 (1H, br. s, NH), 8.78 (1H, br. s, NH), 13.13 (1H, br. s, NH).

¹³C NMR (100 MHz, DMSO-d$_6$) −δ$_C$: 44.94, 52.85, 78.13, 79.33, 94.12, 106.75, 115.67, 115.89, 129.94, 130.02, 154.70, 160.74, 163.16.

¹⁹F NMR—−115.21

NK-46-1

2,2,2-trichloroethyl (2-amino-6-((4-fluorobenzyl)amino)pyridin-3-yl)carbamate

Bluish green solid

Yield—63%

¹H NMR (400 MHz, DMSO-d$_6$) −δ$_H$: 4.57 (2H, d, J=3.05 Hz, CH$_2$Ph), 4.85 (2H, s, CH$_2$), 5.95 (1H, d, J=8.84 Hz, ArH), 7.20 (2H, t, J=8.85 Hz, ArH), 7.42-7.50 (4H, m), 8.36 (1H, br. s, NH), 9.12 (1H, br. s, NH), 13.33 (1H, br. s, NH).

¹³C NMR (100 MHz, DMSO-d$_6$) −δ$_C$: 44.94, 74.45, 94.36, 96.23, 106.24, 115.67, 115.88, 129.97, 130.05, 153.97, 160.74, 163.20.

¹⁹F NMR—−115.19

NK-48-3

Ethyl (6-((4-fluorobenzyl)amino)-4-methylpyridin-3-yl)carbamate

Orange solid

Yield—46%

Rf—0.37 (20:1—DCM:MeOH)

¹H NMR (400 MHz, CDCl$_3$) −δ$_H$: 1.26 (3H, br. s, CH$_2$CH$_3$), 2.15 (3H, s, CH$_3$), 4.17 (2H, q, J=7.1 Hz, CH$_2$CH$_3$), 4.43 (2H, br. s, CH$_2$Ph), 5.62 (1H, br. s, NH), 6.24 (1H, s, ArH), 6.56 (1H, br. s, NH), 7.0 (2H, t, J=8.62 Hz, ArH), 7.30 (2H, t, J=8.20 Hz, ArH), 7.98 (1H, br. s, ArH).

¹³C NMR (100 MHz, CDCl$_3$) −δ$_C$: 14.56, 17.97, 45.66, 61.46, 107.73, 115.34, 115.55, 123.68, 128.84, 128.91, 134.50, 160.81, 162.25.

NK-52-3

Ethyl (2-amino-6-((1-phenylethyl)amino)pyridin-3-yl)carbamate

Bluish green solid
Yield—67%
$^1$H NMR (400 MHz, DMSO-d$_6$) –δ$_H$: 1.21 (3H, t, J=6.18 Hz, CH$_2$CH$_3$), 1.45 (3H, d, J=7.06 Hz, CH$_3$), 4.05 (2H, q, J=7.31 Hz, CH$_2$CH$_3$), 4.17 (1H, q, J=7.12 Hz, CHPh), 7.07-7.22 (4H, m), 7.26-7.32 (4H, m), 7.44 (1H, br. s, NH), 8.55 (1H, br. s, NH), 13.11 (1H, br. s, NH).
$^{13}$C NMR (100 MHz, DMSO-d$_6$) –δ$_C$: 14.91, 21.11, 35.77, 60.96, 107.56, 111.68, 126.80, 127.61, 128.85, 144.68, 147.98, 155.41.

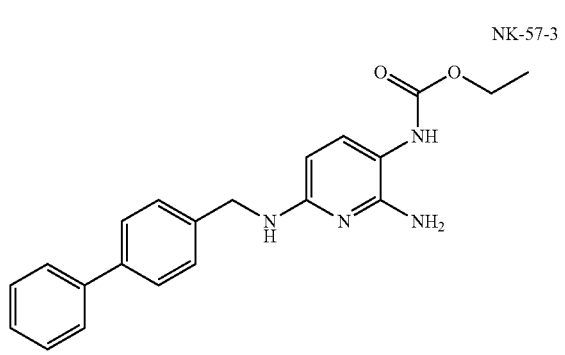 [SMILES: CCOC(=O)Nc1ccc(NCc2ccc(-c3ccccc3)cc2)nc1N]

NK-57-3

Ethyl (6-(([1,1'-biphenyl]-4-ylmethyl)amino)-2-aminopyridin-3-yl)carbamate

Bluish green solid
Yield—33%
$^1$H NMR (400 MHz, DMSO-d$_6$) –δ$_H$: 1.21 (3H, t, J=6.57 Hz, CH$_2$CH$_3$), 4.05 (2H, q, J=6.71 Hz, CH$_2$CH$_3$), 4.61 (2H, d, J=4.40 Hz, CH$_2$Ph), 5.95 (1H, d, J=8.83 Hz, ArH), 7.35-7.50 (7H, m, ArH, —NH), 7.65-7.68 (4H, m, ArH), 8.29 (1H, br. s, NH), 8.54 (1H, br. s, NH), 13.27 (1H, br. s, NH).
$^{13}$C NMR (100 MHz, DMSO-d$_6$) –δ$_C$: 19.94, 45.35, 60.97, 94.19, 107.19, 127.09, 127.31, 127.91, 128.48, 129.39, 137.30, 139.76, 140.25, 143.21, 149.85, 155.52.

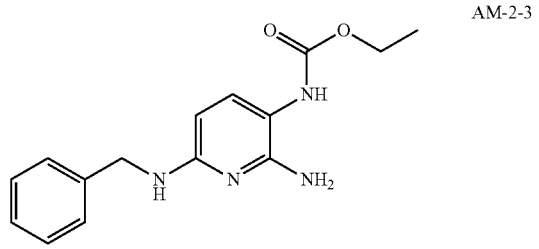 [SMILES: CCOC(=O)Nc1ccc(NCc2ccccc2)nc1N]

AM-2-3

Ethyl (2-amino-6-(benzylamino)pyridin-3-yl)carbamate

Bluish solid
Yield—97%
$^1$H NMR (400 MHz, DMSO-d$_6$) –δ$_H$: 1.21 (3H, t, J=6.68 Hz, CH$_2$CH$_3$), 4.05 (2H, q, J=7.08 Hz, CH$_2$CH$_3$), 4.59 (2H, d, J=3.04 Hz, CH$_2$Ph), 5.94 (1H, d, J=8.85 Hz, ArH), 7.29 (1H, m, ArH), 7.34-7.56 (6H, m), 8.40 (1H, br. s, NH), 8.57 (1H, br. s, NH), 13.45 (1H, br. s, NH).
$^{13}$C NMR (100 MHz, DMSO-d$_6$) –δ$_C$: 14.94, 24.85, 45.72, 60.97, 94.21, 107.06, 127.94, 128.99, 137.94, 143.33, 149.59, 155.50.

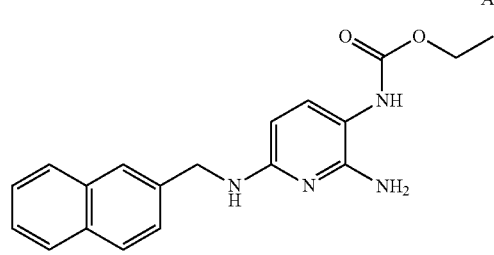

AM-4-3

Ethyl (2-amino-6-((4-methoxybenzyl)amino)pyridin-3-yl)carbamate

Bluish solid
Yield—56%
$^1$H NMR (400 MHz, DMSO-d$_6$) –δ$_H$: 1.21 (3H, t, J=7.05 Hz, CH$_2$CH$_3$), 3.74 (3H, s, CH$_3$), 4.05 (2H, q, J=7.12 Hz, CH$_2$CH$_3$), 4.47 (2H, d, J=4.91 Hz, CH$_2$Ph), 5.92 (1H, d, J=8.78 Hz, ArH), 6.93 (2H, d, J=8.72 Hz, ArH), 7.32-7.47 (4H, m, ArH, NH), 8.72 (1H, br. s, NH), 8.53 (1H, br. s, NH), 13.06 (1H, br. s, NH).
$^{13}$C NMR (100 MHz, DMSO-d$_6$) –δ$_C$: 14.94, 45.21, 55.55, 60.98, 66.81, 94.18, 106.96, 114.40, 129.35, 129.69, 149.67, 155.54, 159.09.

AM-5-3

Ethyl (2-amino-6-((naphthalen-2-ylmethyl)amino)pyridin-3-yl)carbamate

Bluish green solid
Yield—53%
Rf=
$^1$H NMR (400 MHz, MeOD-d$_4$) –δ$_H$: 1.28 (3H, t, J=6.80 Hz, CH$_2$CH$_3$), 4.15 (2H, q, J=7.07 Hz, CH$_2$CH$_3$), 4.84 (2H, s, CH$_2$Ph), 5.82 (1H, d, J=8.36 Hz, ArH), 7.12 (1H, d, J=8.15 Hz, ArH), 7.38 (1H, t, J=8.11 Hz, ArH), 7.45-7.51 (3H, m, ArH), 7.76 (1H, d, J=8.19 Hz, ArH), 7.84-7.88 (1H, m, ArH), 8.05-8.09 (1H, m ArH).
$^{13}$C NMR (100 MHz, CDCl$_3$) –δ$_C$: 14.62, 44.51, 61.50, 96.34, 107.38, 123.46, 125.50, 125.80, 126.31, 128.04, 128.74, 131.42, 133.80, 134.28, 137.34, 153.68, 155.58, 156.50.

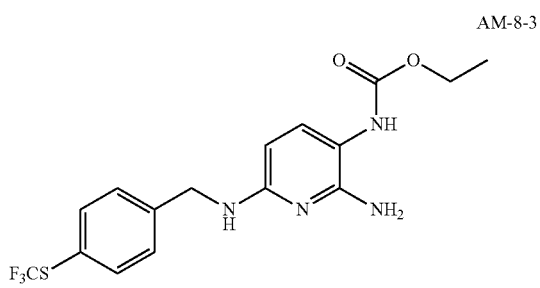

AM-8-3

Ethyl (2-amino-6-((4-((trifluoromethyl)thio)benzyl)amino)pyridin-3-yl)carbamate

Bluish green solid

Yield—45%

$^1$H NMR (400 MHz, DMSO-d$_6$) –δ$_H$: 1.21 (3H, t, J=6.93 Hz, CH$_2$CH$_3$), 4.05 (2H, q, J=7.11 Hz, CH$_2$CH$_3$), 4.66 (2H, d, J=4.88 Hz, CH$_2$Ph), 5.92 (1H, d, J=8.81 Hz, ArH), 7.38-7.49 (2H, m, ArH, NH), 7.33 (2H, d, J=8.23 Hz, ArH), 7.55 (2H, d, J=8.13 Hz, ArH), 8.30 (1H, br. s, NH), 8.55 (1H, br. s, NH), 13.30 (1H, br. s, NH).

$^{13}$C NMR (100 MHz, DMSO-d$_6$) –δ$_C$: 14.93, 45.10, 60.99, 66.81, 93.92, 107.53, 122.19, 128.55, 129.26, 131.61, 136.91, 142.13, 149.64.

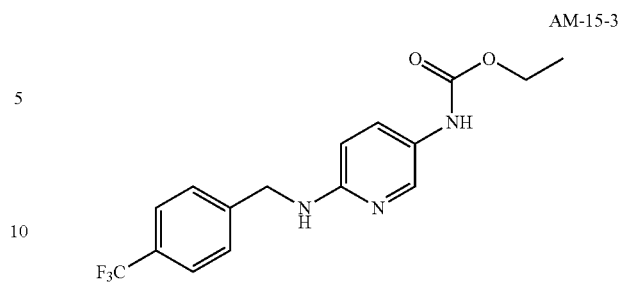

AM-15-3

Ethyl (6-((4-(trifluoromethyl)benzyl)amino)pyridin-3-yl)carbamate

Greenish solid

Yield—

$^1$H NMR (400 MHz, DMSO-d$_6$) –δ$_H$: 1.21 (3H, t, J=7.09 Hz, CH$_2$CH$_3$), 4.07 (2H, q, J=7.10 Hz, CH$_2$CH$_3$), 4.52 (2H, d, J=6.09 Hz, CH$_2$Ph), 6.50 (1H, d, J=8.91 Hz, ArH), 7.02 (1H, t, J=5.94 Hz, NH), 7.46-7.53 (3H, m, ArH), 7.66 (2H, d, J=8.07 Hz, ArH), 7.96 (1H, s, ArH), 9.19 (1H, br. s, NH).

$^{13}$C NMR (100 MHz, DMSO-d$_6$) –δ$_C$: 15.02, 44.44, 60.48, 108.28, 125.48, 126.24, 127.40, 127.71, 128.16, 139.33, 146.54, 154.54, 155.30.

$^{19}$F NMR—–60.69

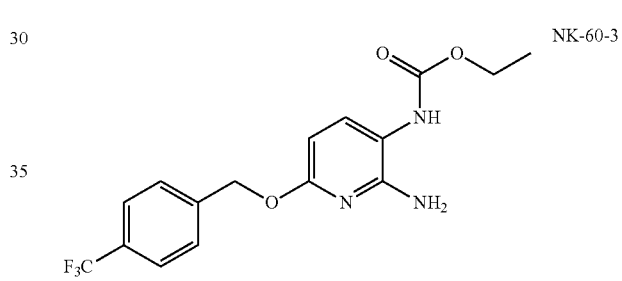

NK-60-3

Ethyl (2-amino-6-((4-(trifluoromethyl)benzyl)oxy)pyridin-3-yl)carbamate

White solid

Yield—44%

$^1$H NMR (400 MHz, DMSO-d$_6$) –δ$_H$: 1.21 (3H, t, J=6.68 Hz, CH$_2$CH$_3$), 4.08 (2H, q, J=7.07 Hz, CH$_2$CH$_3$), 5.39 (2H, s, CH$_2$), 5.88 (2H, br. s, NH$_2$), 6.19 (1H, d, J=8.38 Hz, ArH), 7.58 (1H, d, J=7.61 Hz, ArH), 7.67 (2H, d, J=7.67 Hz, ArH), 7.76 (2H, d, J=8.14 Hz, ArH), 8.67 (1H, br. s, NH).

$^{13}$C NMR (100 MHz, DMSO-d$_6$) –δ$_C$: 14.97, 60.89, 67.66, 95.65, 113.07, 123.32, 125.74, 125.81, 128.72, 138.50, 142.03, 151.70, 155.15.

AM-11-3

Ethyl (2-amino-6-((4-(thiophen-2-yl)benzyl)amino)pyridin-3-yl)carbamate

Bluish solid

Yield—22%

$^1$H NMR (400 MHz, DMSO-d$_6$) –δ$_H$: 1.30 (3H, t, J=7.34 Hz, CH$_2$CH$_3$), 4.15 (2H, q, J=7.06 Hz, CH$_2$CH$_3$), 4.44 (2H, s, CH$_2$Ph), 5.82 (1H, d, J=8.35 Hz, ArH), 7.07-7.13 (2H, m, ArH), 7.34-7.44 (4H, m, ArH), 7.58 (2H, d, J=8.30 Hz, ArH).

$^{13}$C NMR (100 MHz, DMSO-d$_6$) –δ$_C$: 13.53, 44.95, 60.81, 95.82, 106.84, 122.55, 124.12, 125.33, 127.47, 127.64, 132.97, 137.15, 139.62, 143.97, 156.72, 156.86.

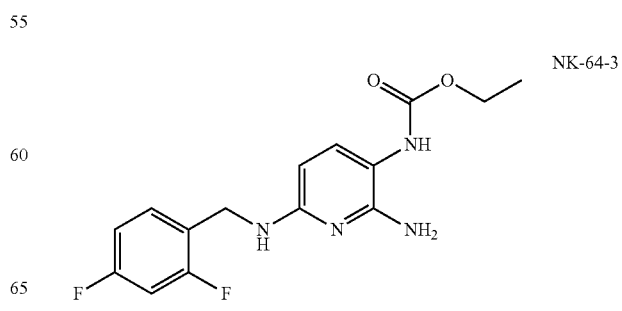

NK-64-3

Ethyl (2-amino-6-((2,4-difluorobenzyl)amino)pyridin-3-yl)carbamate

Green solid
Yield—24%
Rf—0.39 (H:EtOAc=1:1)
$^1$H NMR (400 MHz, CDCl$_3$) –δ$_H$: 1.26 (3H, br. s, CH$_2$CH$_3$), 4.16 (2H, q, J=7.09 Hz, CH$_2$CH$_3$), 4.38 (2H, br. s, CH$_2$Ph), 4.80 (2H, br. s, NH$_2$), 5.16 (1H, br. s, NH), 5.72 (1H, d, J=8.38 Hz, ArH), 6.58 (1H, br. s, NH), 6.78 (2H, t, J=8.43 Hz, ArH), 7.14 (1H, d, J=7.16 Hz, ArH), 7.28 (1H, q, J=8.10 Hz, ArH).
$^{13}$C NMR (100 MHz, CDCl$_3$) –δ$_C$: 14.54, 39.34, 61.54, 95.82, 103.66, 107.68, 111.28, 122.17, 130.16, 137.70, 153.34, 155.72, 160.28, 162.55.
$^{19}$F NMR—-111.89, -115.06

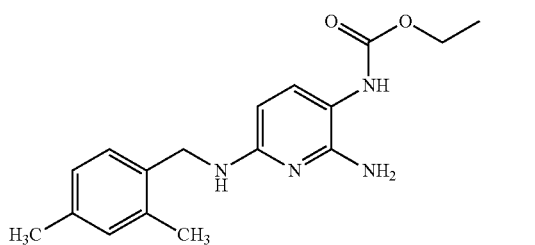

NK-65-3

Ethyl (2-amino-6-((2,4-dimethylbenzyl)amino)pyridin-3-yl)carbamate

Bluish green solid
Yield—33%
Rf—0.36 (DCM:MeOH=20:1)
$^1$H NMR (400 MHz, CDCl$_3$) –δ$_H$: 1.29 (3H, t, J=6.29 Hz, CH$_2$CH$_3$), 2.32 (6H, s, CH$_3$), 4.20 (2H, q, J=7.11 Hz, CH$_2$CH$_3$), 4.33 (2H, d, J=4.84 Hz, CH$_2$Ph), 4.90 (2H, br. s, NH$_2$), 4.97 (1H, t, J=5.15 Hz, NH), 5.77 (1H, d, J=8.44 Hz, ArH), 6.25 (1H, s, ArH), 6.98-7.02 (2H, m, ArH), 7.18 (1H, d, J=7.72 Hz, ArH), 7.22 (1H, br. s, NH).
$^{13}$C NMR (100 MHz, CDCl$_3$) –δ$_C$: 14.58, 18.84, 20.98, 44.46, 61.62, 95.66, 107.27, 126.73, 128.01, 131.28, 133.17, 136.02, 137.13, 138.31, 152.75, 155.44.

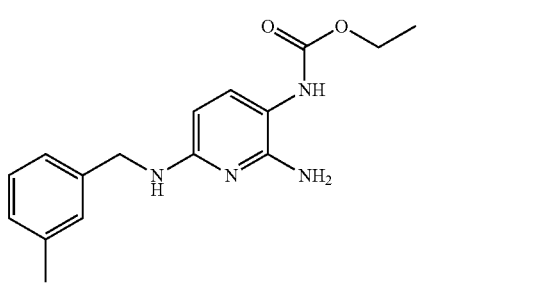

NK-66-3

Ethyl (2-amino-6-((3-methylbenzyl)amino)pyridin-3-yl)carbamate

Greenish solid
Yield—19%
Rf—0.44 (DCM:MeOH=10:1)
$^1$H NMR (400 MHz, CDCl$_3$) –δ$_H$: 1.26 (3H, br. s, CH$_2$CH$_3$), 2.33 (3H, s, CH$_3$), 4.15 (2H, q, J=7.08 Hz, CH$_2$CH$_3$), 4.31 (2H, br. s, CH$_2$Ph), 4.92 (2H, br. s, NH$_2$), 5.38 (1H, br. s, NH), 5.70 (1H, d, J=8.45 Hz, ArH), 6.86 (1H, br. s, NH), 7.06-7.23 (5H, m, ArH).
$^{13}$C NMR (100 MHz, CDCl$_3$) –δ$_C$: 14.57, 21.42, 46.42, 61.56, 95.19, 107.52, 124.27, 127.92, 128.00, 128.51, 138.25, 138.62, 152.48, 154.99, 155.86.

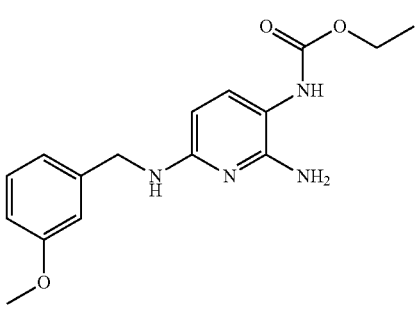

NK-67-3

Ethyl (2-amino-6-((3-methoxybenzyl)amino)pyridin-3-yl)carbamate

Bluish green solid
Yield—54%
$^1$H NMR (400 MHz, CDCl$_3$) –δ$_H$: 1.30 (3H, t, J=6.64 Hz, CH$_2$CH$_3$), 1.77 (3H, s, CH$_3$), 4.21 (2H, q, J=7.10 Hz, CH$_2$CH$_3$), 4.44-4.48 (4H, m), 4.78 (1H, t, J=6.21 Hz, NH), 5.78 (1H, d, J=8.32 Hz, ArH), 6.00 (1H, br. s, NH), 7.11-7.17 (2H, m, ArH), 7.21 (1H, s, ArH), 7.28 (1H, ArH), 7.36 (1H, t, J=7.83, ArH).
$^{13}$C NMR (100 MHz, CDCl$_3$) –δ$_C$: 14.92, 44.99, 60.99, 93.96, 107.53, 119.24, 120.29, 120.36, 121.79, 126.91, 130.98, 141.10, 148.97, 149.62, 155.48.

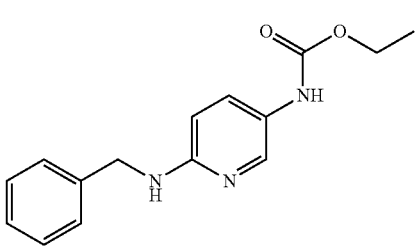

NK-69-3

Ethyl (6-(benzylamino)pyridin-3-yl)carbamate

Yield—26%
$^1$H NMR (400 MHz, DMSO-d$_6$) –δ$_H$: 1.24 (3H, t, J=7.09 Hz, CH$_2$CH$_3$), 4.14 (2H, q, J=7.10 Hz, CH$_2$CH$_3$), 4.64 (2H, br. s, CH$_2$Ph), 7.14 (1H, d, J=9.54 Hz, ArH), 7.30-7.34 (1H, m, ArH), 7.37-7.44 (4H, m, ArH), 7.88 (1H, dd, J=7.45 Hz, 2.11 Hz, ArH), 8.11 (1H, s, ArH), 9.08 (1H, br. s, NH), 9.92 (1H, br. s, NH).
$^{13}$C NMR (100 MHz, DMSO-d$_6$) –δ$_C$: 19.02, 45.76, 56.47, 114.34, 126.81, 128.10, 128.21, 129.07, 136.82, 137.16, 149.89, 154.06.

NK-70-3

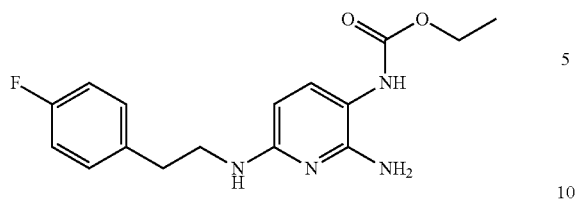

Ethyl (2-amino-6-((4-fluorophenethyl)amino)pyridin-3-yl)carbamate

Bluish green solid
Yield—33%

$^1$H NMR (400 MHz, DMSO-$d_6$) –$\delta_H$: 1.22 (3H, t, J=6.78 Hz, CH$_2$CH$_3$), 2.86 (2H, t, J=7.36 Hz, CH$_2$), 3.56 (2H, q, J=7.10 Hz, CH$_2$), 4.06 (2H, q, J=7.00 Hz, CH$_2$CH$_3$), 5.97 (1H, d, J=8.79 Hz, ArH), 7.13 (2H, t, J=8.93 Hz, ArH), 7.35-7.48 (4H, m, ArH, NH), 7.92 (1H, br. s, NH), 8.53 (1H, br. s, NH), 12.98 (1H, br. s, NH).

$^{13}$C NMR (100 MHz, DMSO-$d_6$) –$\delta_C$: 14.95, 34.00, 43.73, 60.96, 94.27, 106.50, 115.36, 115.57, 131.14, 131.22, 135.19, 160.23, 162.63.

TABLE 3

Predicted MPO Score (brain penetration).

| Molecule ID | clogP | clogD (at pH 7.4) | TPSA$^a$ | MW | HBD$^b$ | pKa (basic) | MPO Score$^c$ |
|---|---|---|---|---|---|---|---|
| NK-1-4 (Flupirtine) | 2.67 | 2.32 | 89.27 | 304.13 | 3 | 7.5 | 5.07 |
| NK-3-1 | 2.31 | 1.96 | 89.27 | 290.29 | 3 | 7.5 | 5.25 |
| NK-4-3 | 3.13 | 2.78 | 89.27 | 320.77 | 3 | 7.5 | 4.69 |
| NK-8-1 | 3.56 | 3.21 | 89.27 | 323.37 | 3 | 7.5 | 4.25 |
| NK-10-1 | 4.04 | 3.69 | 89.27 | 366.39 | 3 | 7.5 | 3.55 |
| NK-12-1 | 3.04 | 2.69 | 89.27 | 316.33 | 3 | 7.5 | 4.80 |
| NK-13-1 | 3.37 | 3.02 | 89.27 | 332.37 | 3 | 7.5 | 4.39 |
| NK-16-3 | 3.4 | 3.05 | 89.27 | 354.33 | 3 | 7.5 | 4.25 |
| NK-16-4 | 3.05 | 2.7 | 89.27 | 340.3 | 3 | 7.5 | 4.67 |
| NK-16-6 | 3.78 | 3.43 | 89.27 | 366.39 | 3 | 7.5 | 3.81 |
| NK-17-3 | 4.28 | 3.93 | 89.27 | 422.33 | 3 | 7.5 | 3.03 |
| NK-21-1 | 3.16 | 2.81 | 89.27 | 338.77 | 3 | 7.5 | 4.57 |
| NK-22-13 (Retigabine) | 2.7 | 2.7 | 76.38 | 303.33 | 3 | 3.99 | 4.88 |
| NK-23-1 | 2.98 | 2.63 | 89.27 | 338.77 | 3 | 7.5 | 4.74 |
| NK-30-2 | 3.22 | 3.22 | 76.38 | 317.36 | 3 | 3.99 | 4.44 |
| NK-31-3 | 2.9 | 2.9 | 63.25 | 289.31 | 2 | 5.56 | 5.05 |
| JG-4-5 | 3.51 | 3.16 | 89.27 | 332.79 | 3 | 7.5 | 4.25 |
| JG-32-3 | 3.04 | 2.69 | 89.27 | 300.36 | 3 | 7.5 | 4.88 |
| JG-33-4 | 3.96 | 3.61 | 98.5 | 370.33 | 3 | 7.5 | 3.33 |
| JG-34-4 | 3.4 | 3.05 | 89.27 | 354.33 | 3 | 7.5 | 4.25 |
| JG-35-4 | 4.62 | 4.27 | 89.27 | 457.66 | 3 | 7.5 | 2.65 |
| JG-36-4 | 2.82 | 2.44 | 89.27 | 300.36 | 3 | 7.55 | 5.03 |
| JG-38-4/AM-9-3 | 3.55 | 3.2 | 89.27 | 372.32 | 3 | 7.55 | 4.01 |
| JG-41-4 | 1.22 | 0.96 | 89.71 | 266.3 | 2 | 7.31 | 5.50 |
| JG-48-6 | 4.51 | 4.51 | 76.38 | 365.4 | 3 | 3.97 | 3.17 |
| NK-34-2 | 4.55 | 4.55 | 76.38 | 359.44 | 3 | 3.99 | 3.18 |
| NK-39-3 | 3.27 | 3.27 | 63.25 | 285.34 | 2 | 5.56 | 4.73 |
| NK-40-3 | 3.4 | 3.05 | 89.27 | 354.33 | 3 | 7.5 | 4.25 |
| NK-41-1 | 3.97 | 3.62 | 89.27 | 352.36 | 3 | 7.5 | 3.69 |
| NK-42-1 | 4.53 | 4.18 | 89.27 | 360.43 | 3 | 7.5 | 3.18 |
| NK-43-1 | 5.5 | 5.15 | 89.27 | 454.5 | 3 | 7.5 | 2.48 |
| NK-45-1 | 2.54 | 2.19 | 89.27 | 314.31 | 3 | 7.5 | 5.08 |
| NK-46-1 | 3.89 | 3.54 | 89.27 | 407.66 | 3 | 7.5 | 3.50 |
| NK-48-3 | 3.42 | 3.37 | 63.25 | 303.33 | 2 | 6.5 | 4.59 |
| NK-52-3 | 2.94 | 2.61 | 89.27 | 300.36 | 3 | 7.47 | 4.94 |
| NK-57-3 | 4.17 | 3.82 | 89.27 | 362.43 | 3 | 7.5 | 3.44 |
| AM-2-3 | 2.53 | 2.18 | 89.27 | 286.33 | 3 | 7.5 | 5.16 |
| AM-4-3 | 2.37 | 2.02 | 98.5 | 316.36 | 3 | 7.5 | 4.88 |
| AM-5-3 | 3.52 | 3.17 | 89.27 | 336.39 | 3 | 7.5 | 4.22 |

TABLE 3-continued

Predicted MPO Score (brain penetration).

| Molecule ID | clogP | clogD (at pH 7.4) | TPSA[a] | MW | HBD[b] | pKa (basic) | MPO Score[c] |
|---|---|---|---|---|---|---|---|
| AM-8-3 | 4.5 | 4.15 | 89.27 | 386.39 | 3 | 7.5 | 2.99 |
| AM-11-3 | 3.95 | 3.6 | 89.27 | 368.45 | 3 | 7.5 | 3.63 |
| AM-15-3 | 3.64 | 3.63 | 63.25 | 339.31 | 2 | 5.56 | 4.17 |
| NK-60-3 | 3.77 | 3.77 | 86.47 | 355.31 | 2 | 3.81 | 3.95 |
| NK-64-3 | 2.81 | 2.46 | 89.27 | 322.31 | 3 | 7.5 | 4.91 |
| NK-65-3 | 3.55 | 3.2 | 89.27 | 314.38 | 3 | 7.5 | 4.30 |
| NK-66-3 | 3.04 | 2.69 | 89.27 | 300.36 | 3 | 7.5 | 4.88 |
| NK-67-3 | 2.37 | 2.02 | 98.5 | 316.36 | 3 | 7.5 | 4.88 |
| NK-69-3 | 2.76 | 2.76 | 63.25 | 271.31 | 2 | 5.56 | 5.12 |
| NK-70-3 | 2.96 | 2.58 | 89.27 | 318.35 | 3 | 7.55 | 4.87 |

[a]Total Polar Surface Area
[b]Hydrogen Bond Donors
[c]Multi-Parameter Optimization It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of treating a subject afflicted with a neurodegenerative disorder or disease comprising:

determining that the subject is in need of treatment for the neurodegenerative disorder or disease; and administering to the subject an amount of an effective amount of a compound comprising a flupirtine derivative selected from at least one of:

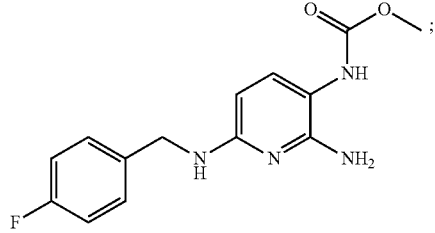

NK-3-1

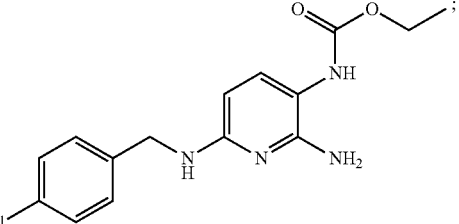

NK-4-3

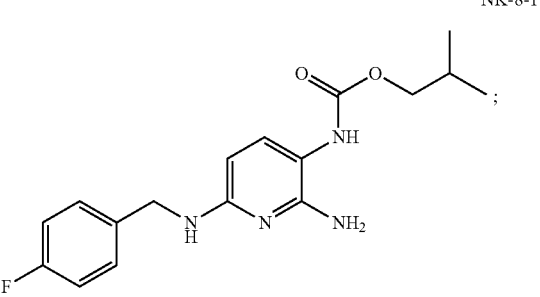

NK-8-1

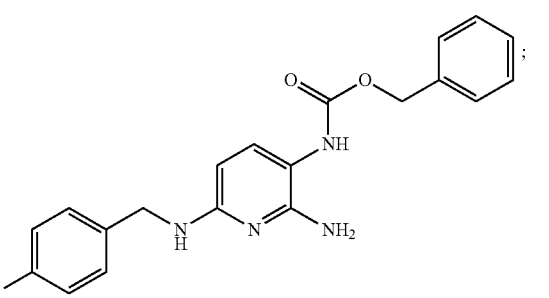

NK-10-1

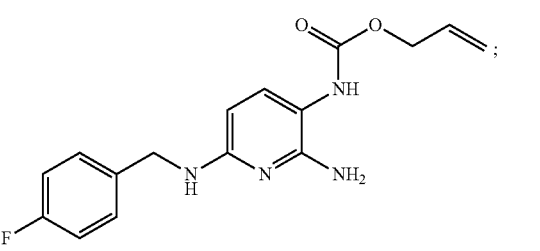

NK-12-1

-continued

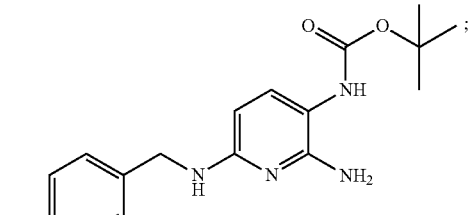

NK-13-1

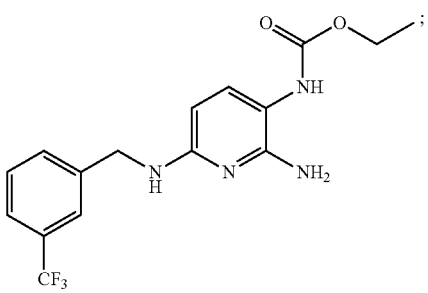

NK-16-3

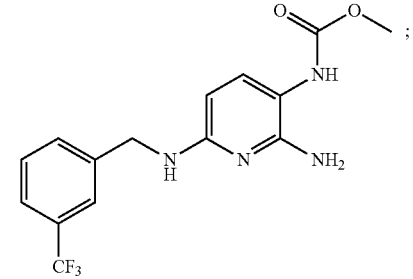

NK-16-4

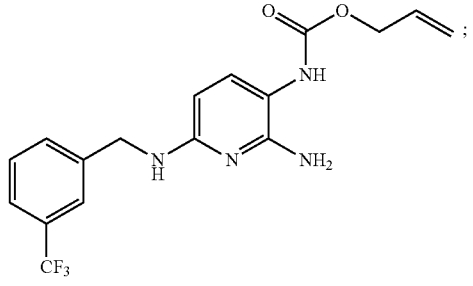

NK-16-6

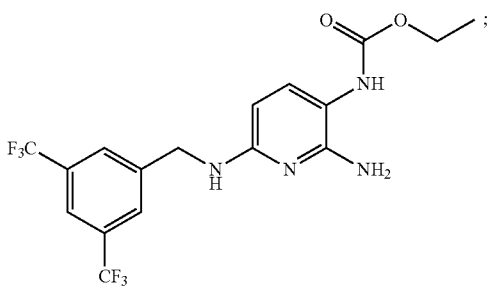

NK-17-3

-continued
NK-21-1
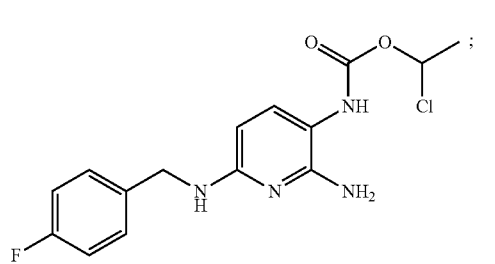
NK-22-6
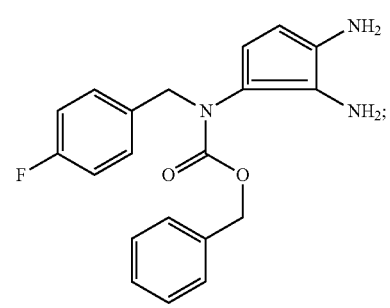
NK-22-13
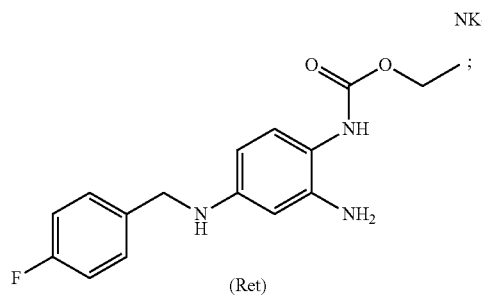
(Ret)
NK-23-1
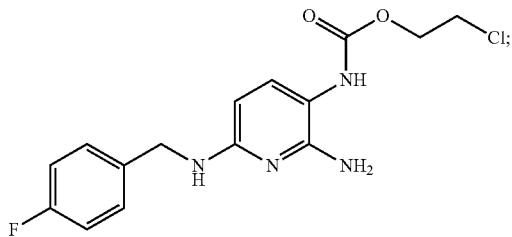
NK-30-2
NK-31-3
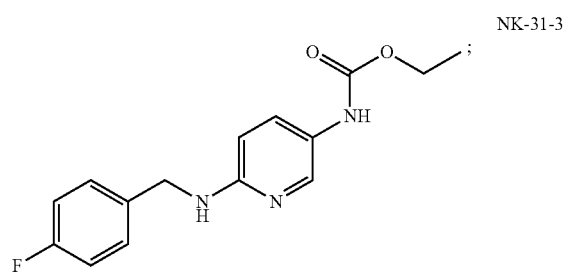
-continued
NK-34-2
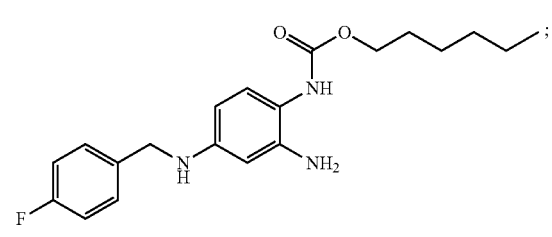
NK-39-3
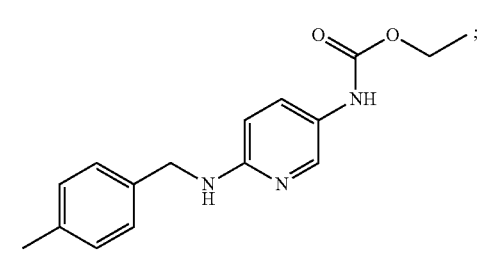
NK-40-3
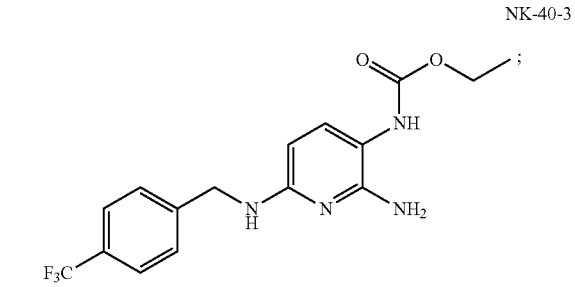
NK-41-1
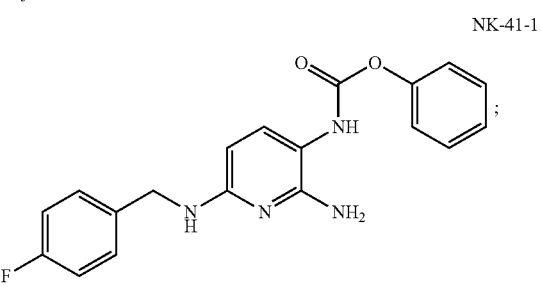
NK-42-1
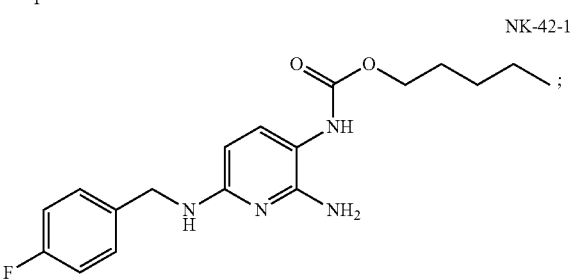
NK-43-1
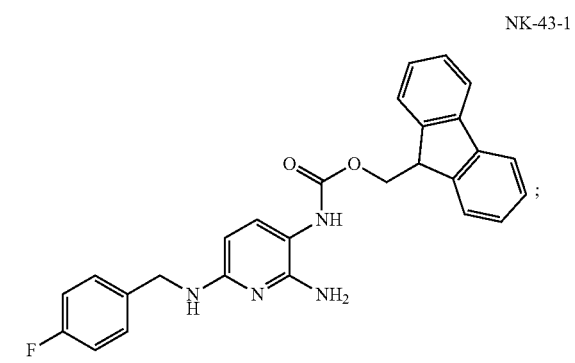

-continued

NK-45-1

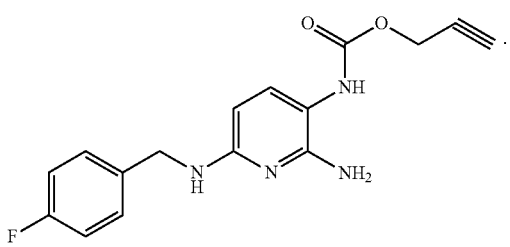

2. The method of claim 1, wherein the amount of the compound is effective to reduce a symptom of the neurodegenerative disorder or disease in the subject.

3. The method of claim 1, wherein the neurodegenerative disorder or disease is a brain atrophy, neuronal dysfunction, neuronal injury, neuronal degeneration, neuronal apoptosis, risk for confirmed progression, deterioration of visual function, fatigue, impaired mobility, cognitive impairment, or reduction of brain volume.

4. The method of claim 1, wherein the amount of compound is effective to reduce cognitive impairment.

5. The method of claim 1, further comprising adapting the composition for oral, intravenous, cutaneous, peritoneal, parenteral, rectal, pulmonary, nasal, administration.

6. The method of claim 1, further comprising adapting the composition for slow release form or an immediate release form.

7. The method of claim 1, further comprising combining the composition with a pharmaceutically acceptable excipient.

8. The method of claim 1, further comprising combining the composition with the pharmaceutically acceptable excipient that is selected from at least one of lactose, lactose monohydrate, starch, isomaltose, mannitol, sodium starch glycolate, sorbitol, lactose spray dried, lactose anhydrous, or a combination thereof.

9. The method of claim 1, further comprising adapting the composition for administration daily, more often than once daily, or less often than once daily.

10. The method of claim 1, further comprising adapting the composition for administration from 10-1000 mg/day.

11. The method of claim 1, further comprising adapting the composition for administration from 50-500 mg/day, or 100-400 mg/day.

\* \* \* \* \*